United States Patent
Lulla et al.

(10) Patent No.: US 7,189,540 B2
(45) Date of Patent: Mar. 13, 2007

(54) OPTIMIZED RECOGNITION SITE OF THE ALPHAVIRUS NON-STRUCTURAL PROTEASE FOR TAG REMOVAL AND SPECIFIC PROCESSING OF RECOMBINANT PROTEINS

(75) Inventors: Aleksei Lulla, Tartu (EE); Kairit Tints, Tartu (EE); Signe Tobi, Tartu (EE)

(73) Assignee: Quattromed AS, Tartu (EE)

( * ) Notice: Subject to any disclaimer, the term of this patent is extended or adjusted under 35 U.S.C. 154(b) by 0 days.

(21) Appl. No.: 11/157,360

(22) Filed: Jun. 21, 2005

(65) Prior Publication Data

US 2005/0282254 A1    Dec. 22, 2005

Related U.S. Application Data

(60) Provisional application No. 60/581,579, filed on Jun. 21, 2004.

(51) Int. Cl.
   *C12P 21/06* (2006.01)
(52) U.S. Cl. .................. 435/69.1; 536/23.1
(58) Field of Classification Search .......... 435/69.1; 536/23.1
   See application file for complete search history.

(56) References Cited

FOREIGN PATENT DOCUMENTS

WO    WO 92/10578    *    6/1992

OTHER PUBLICATIONS

Kohno et al., Semliki Forest virus-based DNA expression vector: transient protein production followed by cell death, Gene Therapy (1998), 5, p. 415-418.☐☐.*

Liljestrom et al., A new generation of animal cell expression vectors based on the Semliki Forest virus replicon, Bio/Technology Dec. 9, (1991), 1356-1361.*

Vasiljeva L. et al. 2000 Identification of Novel function of the alphavirus capping . . . J. of Biol. Chem. 275(23): 1728-1787.

Vasiljeva L et al. 2001. Site-specific protease activity of hte carboxyl . . . J. of Biol Chem. 276(33) 30786-30793.

Merits A. et al. 2001. Proteolytic processing of Semliki Forest Virus . . . J. Gen Vir. 82: 765-773.

* cited by examiner

*Primary Examiner*—Robert A. Wax
*Assistant Examiner*—Agnes Rooke
(74) *Attorney, Agent, or Firm*—Dodds and Associates; Susanne Somersalo

(57) ABSTRACT

The present invention discloses highly efficient novel recognition sites for Pro39 protease. The invention further provides a wide range of conditions for protein purification and modification with the novel recognition sites. The invention even further provides expression vectors for expression of fusion proteins in cells and method to purify fusion proteins.

15 Claims, 25 Drawing Sheets

```
5'  GA TCT CAC CAT CAC CAT CAC CAT GAC GTC CTG CGA CTA GGC CGC GCG GGT GCC GGC ATT TTC TCC TCG GGA TCC A
3'                                                                                                      
3'  A GTG GTA GTG GTA GTG GTA CTG CAG GAC GCT GAT CCG GCG CGC CCA CGG CCG TAA AAG AGG AGC CCT AGG TTC GA 5'
    G  S  H...H...H...H...H...H   D   V   L   R   L   G   R   A   G   A   G   I   F   S   S   G   S   K   L
                                 -10  -9  -8  -7  -6  -5  -4  -3  -2  -1  +1  +2  +3  +4  +5
``` modified (Y →G) SFV protease recognition site -10/+5

FIG 16

5' GA TCT CAC CAT CAC CAT CAC CAT GAC GTC CTG CGA CTA GGC CGC GCG GGT GCC CGC ATT TTC TCC TCG GGA TCC A         3'
3'    A GTG GTA GTG GTA GTG GTA CTG CAG GAC GCT GAT CCG GCG CGC CCA CGG GCG TAA AAG AGG AGC CCT AGG TTC GA 5'
   G  S  H....H....H....H....H....H   D   V   L   R   L   G   R   A   G   A   R   I   F   S   S   G   S   K   L
                                     -10 -9  -8  -7  -6  -5  -4  -3  -2  -1  +1  +2  +3  +4  +5 modified (Y →R) SFV protease recognition site -10/+5

FIG. 17

```
   1 gatcttttc cctctgccaa aaattatgg gacatcatga tgccccttga gcatctgact tctggctaat aaaggaaatt tatttcatt gcuutagtgt gttggaattt tttgtgtctc
 121 tcactcggaa agacatatgg gagggcaaat cattuuuac atcagaatga gtattggtt tagagttgg caacatatgc catatgciyg ctgccatgaa caaaggtggc tataaagagg
 241 tcatcagtat atgaaacagc ccccctgctgt ccattccita ttccatagaa aagccttgac ttgaggrtag attttttta tattttgttt tgtgtattt tttcttttaa catccctuaa
 361 attttccctta catgtttac tagccagatt tttcctccte luctgactac tcccagtcat agctgtccct cttctcttat gaactcgagc cttttgcaaa agcctaggcc tccaaaautg
 481 cctcctcact acitctcgaa tagctcgaga gccgaggggg cctcggcctc tgcataaata gtcagccatg gggciyagaa tgggcggaac tgggccguugt taggggcggg
 601 atggggcgag ttaggggcgg gactutggtt gctgucluaat tgagatgctg cattaatgaa tcgccaacg cgcggggaga ggcgggttgc gtattgggcg ctcttccgct tctcgctca
 721 ctgactcgct ggctcggtc gttcggctgc ggcgagtcgt atcagctcac tcaaaggcgg taatacgttt atccacagaa tcaggggata acgcaggaaa gaacatgtgA gcaaaaggcc
 841 agcaaaaggc cuggaaccgt aaaaaggccg cgttgctgcc ggcgttttcc ataggctccgc gtccgacct gcgtcttcca cggataactg tccgcccctt tccttcggg aagcgtggcg clttctcata
 961 tataaagata ccaggcgttt cccccctgaa gctcccctcgt gcgctctcct ggcgtctcct gttccgaccc tgccgcttac cggatactg tccgcctttc cggataccg ccttatccgg taactatcgt ctlgagtcca
1081 gctcacgctg tagtgatctc agttcggtgt aggtcgttcg ctccaagctg ggctgtgtgc acgaacccc cgttcagccc cgttcagcc gaccgtgcg ccttatccgg taactatgac ggctaactac ggctacacta
1201 acccgguang, acaagactta tcgccactgg cagtcgccac tggtaacagg attagcagag caaagagttg gtagctcltg atccggcaaa caaaccuccg ctggtagcgg tggttttt gttgcaagc
1321 gaaggacagt uiltggtatc tgccgtctgc tgaagccagt taccttcgga aaaagagttg gtagctcltt tctacggggt ctigacgctca gtggaacgaa aactcuwgtt aaggggattt ggtcatgaga ttatcaaaaa
1441 agcagattac gcgcagaaaa aaaggatctc aagaAgatct tttgatctt tctacggggt ctigacgctca gtggaacgaa aactcuwgtt aaggggattt ggtcatgaga ttatcaaaaa
1561 ggatcttcac ctugatctt ttaaattaaa aatgaagttt taaatcaatc taaagtatul atggaliuuac ttggtctgac agttaccaat gcttaatcag tgaggcacct atctcagcga
1681 tctgtctatt tcgttcatcc atagttgcct gactcccgt cgtgtagata actacgatac ggguiggctt accatcggc cccagtgctg caatgatacc gcgagaccca cgctcaccgg
1801 ctccagattt atctugcaata aaccagccag ccggAaggc cgagcgcaga agtggtccly caactttatc cgcctccatc cagtctutta attgttccg ggaagctaga gtaagtagtt
1921 cgccagttaa tagtttgcgc aacgttgttg ccattgctac aggcatcgtg gtgtcacgct cgtcgtttgg tatggcttca ttcagctcca gttccgaaacg atcaaggcga gttacatgat
2041 ccccccatgt gtgcaaaaaa gcggttagct cctteggtcc tccgatcgtt gtcagaagta agttggccgc agtgttatca ctcatggtta tggcagcact acgggataat accgcgccac
2161 tgccatccgt aagatgctt tctgtgactg gtgagtatc aaccaagtca ttctgagaat agtgtatgcg gcgaccgagt tgctcttgcc cggcgtcaat acggataaat agtgtcaccc tcgtcacc aactgatctt
2281 atagtgaac tttaaaagtg ctcatcattg gaaaacgttc ttcggggcga aaactctcaa ggatcttacc gctgttgaga tccagttcga tgtaacccac tcgtgcaccc acataccgcg caaaaaaggg
2401 caacatcttt tacttccacc agcgtttctg ggtgagcaaa aacaggaagg caaaatgccg caaaaaaggg aataaggggg acacygaaat gttgaatact catacctcc cttttcaat
2521 attattgaag caattacag ggttattgtc acattaacct ataaaaatag gcgtatcacg aggccctttc gtcggcgcg gttttggcgg gtgttggcgg gtgtgggcg tacctcgaca catgcagctc coggagacgg
2641 aagaaaccat tattatcatg acattaacct ataaaaatag gcgtatcacg aggccctttc gtcggcgcg gttttggcgg gtgttggcgg gtgtgggcg tacctcgaca catgcagctc coggagacgg
2761 tcacagcttg tctgtaagcg gatgccggga gcagttcagc ccgtcagggc gcgtcagtgg gctgttgcgg gtgtggggcg tgcttaact atgcggcatc agagcagatt gtactgagag
2881 tgcaccatat gcggtgtgaa atacccgcaca gatgcgtaag gagaaaatac cgcatcagga gaaaaatac gttaatatttt tgttaaaatt cccgttaaat tcgcttcatt
```

Fig. 18

```
3001 ttttaaccaa taggccgaaa tcggcaaaat cccttataaa tcaaaagaat agaccgagat agggttgagt gttgttccag tttggaacaa gagtccacta ttaaagaacg tggactccaa
3121 cgtcaaaggg cgaaaaaccg tctatcaggg cgatggccca ctacgtgaac catcaccctg ggtgcctaa atcaagtttt ttggggtcga ggtgcctgaa agcactaaat cggaaccta aagggagccc
3241 ccgatttaga gcttgacggg gaaagccggc gaacgtggcg agaaaggaag ggaagaaagc gaaaggagcg ggcgtaggg cgctggcaag tgtagcggtc acgctgcgcg taaccaccac
3361 acccgcccgcg cttaatgcgc cgctacaggg cgcgtgcgc cattcgccat tcaggctgcg caactgttgg gaagggcgat cggtgcgggc ctcttcgcta ttacgccagc tggcgaaagg
3481 gggatgtgct gcaaggcgat taagttgggt aacgccaggg ttttcccagt cacgacgttg taaaacgacg gccagtgaat tgtaatacga ctcactatag ggcgaattcg agctcgcccc
3601 gttacataac ttacggtaaa tggcccgcct ggctgaccgc ccaacgaccc ccgccattg acgtcaataa tgacgtatgt tcccatagta acgccaatag ggactttcca ttgacgtcaa
3721 tgggtggagt atttacggta aactgcccac ttggcagtac atcaagtgta tcatatgcca agtacgcccc ctattgacgt caatgacggt aaatggcccg cctggcatta tgcccagtac
3841 atgaccttat gggactttcc tacttggcag tacatctacg tattagtcat cgctattacc atggtgatgc ggttttggca gtacatcaat gggcgtggat agcggtttga ctcacgggga
3961 tttccaagtc tccaccccat tgacgtcaat gggagtttgt tttggcacca aaatcaacgg gactttccaa aatgtcgtaa caactccgcc ccattgacgc aaatgggcgg taggcgtgta
4081 cggtgggagg tctatataag cagagctcgt ttagtgaacc gtcagatcgc ctggagacgc catccacgct gttttgacct ccatagaaga caccgggacc gatccagcct ccggggatc
4201 ttgtggcgt gaaactcccg cactcttcg gccagcgccc tgagaagcgt ctaggacgt cgtaggcctt ctagagccat ggttcaagt acttcttctg atttagaga tcgcggatcc aagcttccg
4321 ggctgcaggg taccagatcc tgagaacttc agggtgagtt tgggacccct catgataatt ttgttttctt cacttctac tctgttgaca accattgct cctcttatt tcttcatt ttctgtaact
4441 tttagaatgg gaagatgtcc ctttatcac ctttgatgtcc ctgtatcac cttgatgatta tcagattgta agtactttct ctaatcactt tttttcaag gcaatcaggg tatattatat
4561 tttcgttaa acttagctt gcattgtaa cagagacaatt gttaatta aatgataagg tagaatatt ctgcatataa attctggctg gcgtgaaat atttcttattg gtagaaacaa ctacatcctg
4681 tgtacttcag cacagttta gagaacaatt gttaatta aatgataagg tagaatatt ctgcatataa attctggctg gcgtgaaat atttcttattg gtagaaacaa ctacatcctg
4801 gtcatcatcc tgccttctc tttatggtta caatgatata cactgtttga gatgaggata aaatactctg agtccaaacc gggccctct gctaaccatg ttcatgcctt cttcttttc
4921 ctacagtcc tgggcaacgt gctgttgtt gtgctgtctc atcattttgg caaagaattc actcctcagg tgcaggctgc ctatcagaag gtggtggctg gtgtggccaa tgccctggct
5041 cacaaatacc actga
```

Fig. 18 cont.

SEQUENCE LISTING

```
<160> NUMBER OF SEQ ID NOS: 33

<210> SEQ ID NO 1
<211> LENGTH: 15
<212> TYPE: PRT
<213> ORGANISM: artificial
<220> FEATURE:
<223> OTHER INFORMATION: Alphavirus non-structural polyprotein P1234
<220> FEATURE:
<221> NAME/KEY: MISC_FEATURE
<222> LOCATION: (1)..(15)
<223> OTHER INFORMATION: 10/5 recognition site variant
<220> FEATURE:
<221> NAME/KEY: MISC_FEATURE
<222> LOCATION: (11)..(11)
<223> OTHER INFORMATION: +1 amino acid

<400> SEQUENCE: 1

Asp Val Leu Arg Leu Gly Arg Ala Gly Ala Tyr Ile Phe Ser Ser
1               5                   10                  15

<210> SEQ ID NO 2
<211> LENGTH: 11
<212> TYPE: PRT
<213> ORGANISM: artificial
<220> FEATURE:
<223> OTHER INFORMATION: alphavirus nonstructural polyprotein P1234
<220> FEATURE:
<221> NAME/KEY: MISC_FEATURE
<222> LOCATION: (1)..(11)
<223> OTHER INFORMATION: 6/5 recognition site variant
<220> FEATURE:
<221> NAME/KEY: MISC_FEATURE
<222> LOCATION: (7)..(7)
<223> OTHER INFORMATION: +1 amino acid

<400> SEQUENCE: 2

Leu Gly Arg Ala Gly Ala Tyr Ile Phe Ser Ser
1               5                   10
```

-continued

<210> SEQ ID NO 3
<211> LENGTH: 15
<212> TYPE: PRT
<213> ORGANISM: artificial sequence
<220> FEATURE:
<223> OTHER INFORMATION: alphavirus non structural polyprotein P1234
<220> FEATURE:
<221> NAME/KEY: MISC_FEATURE
<222> LOCATION: (1)..(15)
<223> OTHER INFORMATION: 10/R5 recognition site
<220> FEATURE:
<221> NAME/KEY: MISC_FEATURE
<222> LOCATION: (11)..(11)
<223> OTHER INFORMATION: +1 amino acid

<400> SEQUENCE: 3

```
Asp Val Leu Arg Leu Gly Arg Ala Gly Ala Arg Ile Phe Phe Ser
1               5                   10                  15
```

<210> SEQ ID NO 4
<211> LENGTH: 11
<212> TYPE: PRT
<213> ORGANISM: artificial
<220> FEATURE:
<223> OTHER INFORMATION: alphavirus non structural polyprotein P1234
<220> FEATURE:
<221> NAME/KEY: MISC_FEATURE
<222> LOCATION: (1)..(11)
<223> OTHER INFORMATION: 6/R5 recognition site variant
<220> FEATURE:
<221> NAME/KEY: MISC_FEATURE
<222> LOCATION: (7)..(7)
<223> OTHER INFORMATION: +1 amino acid

<400> SEQUENCE: 4

```
Leu Gly Arg Ala Gly Ala Arg Ile Phe Ser Ser
1               5                   10
```

<210> SEQ ID NO 5
<211> LENGTH: 15
<212> TYPE: PRT
<213> ORGANISM: artificial
<220> FEATURE:
<223> OTHER INFORMATION: alphavirus nonstructural polyprotein P1234
<220> FEATURE:
<221> NAME/KEY: MISC_FEATURE
<222> LOCATION: (1)..(15)
<223> OTHER INFORMATION: 10/G5 recognition site variant
<220> FEATURE:
<221> NAME/KEY: MISC_FEATURE
<222> LOCATION: (11)..(11)
<223> OTHER INFORMATION: +1 amino acid

<400> SEQUENCE: 5

```
Asp Val Leu Arg Leu Gly Arg Ala Gly Ala Gly Ile Phe Ser Ser
1               5                   10                  15
```

<210> SEQ ID NO 6
<211> LENGTH: 11
<212> TYPE: PRT
<213> ORGANISM: artificial
<220> FEATURE:
<223> OTHER INFORMATION: alphavirus non structural polyprotein P1234
<220> FEATURE:
<221> NAME/KEY: MISC_FEATURE
<222> LOCATION: (1)..(11)
<223> OTHER INFORMATION: 6/G5 recognition site variant
<220> FEATURE:
<221> NAME/KEY: MISC_FEATURE
<222> LOCATION: (7)..(7)
<223> OTHER INFORMATION: +1 amino acid

```
<400> SEQUENCE: 6

Leu Gly Arg Ala Gly Ala Gly Ile Phe Ser Ser
1               5                   10

<210> SEQ ID NO 7
<211> LENGTH: 10
<212> TYPE: PRT
<213> ORGANISM: artificial
<220> FEATURE:
<223> OTHER INFORMATION: Bovine papilloma virus
<220> FEATURE:
<221> NAME/KEY: MISC_FEATURE
<222> LOCATION: (1)..(10)
<223> OTHER INFORMATION: E2Tag recognition site

<400> SEQUENCE: 7

Ser Ser Thr Ser Ser Asp Phe Arg Asp Arg
1               5                   10

<210> SEQ ID NO 8
<211> LENGTH: 10
<212> TYPE: PRT
<213> ORGANISM: artificial
<220> FEATURE:
<223> OTHER INFORMATION: Bovine papillomavirus
<220> FEATURE:
<221> NAME/KEY: MISC_FEATURE
<222> LOCATION: (1)..(10)
<223> OTHER INFORMATION: E4Tag recognition site

<400> SEQUENCE: 8

Gly Thr Thr Gly His Tyr Ser Val Arg Asp
1               5                   10

<210> SEQ ID NO 9
<211> LENGTH: 10
<212> TYPE: PRT
<213> ORGANISM: artificial
<220> FEATURE:
<223> OTHER INFORMATION: synthetic sequence

<400> SEQUENCE: 9

Leu Glu His His His His His His His His
1               5                   10

<210> SEQ ID NO 10
<211> LENGTH: 37
<212> TYPE: PRT
<213> ORGANISM: artificial
<220> FEATURE:
<223> OTHER INFORMATION: alphavirus non structural polyprotein P1234
<220> FEATURE:
<221> NAME/KEY: MISC_FEATURE
<222> LOCATION: (1)..(37)
<223> OTHER INFORMATION: 20/20 recognition site variant
<220> FEATURE:
<221> NAME/KEY: MISC_FEATURE
<222> LOCATION: (20)..(20)
<223> OTHER INFORMATION: +1 amino acid

<400> SEQUENCE: 10

Ser Gly Ile Thr Phe Gly Asp Ph

-continued

```
<210> SEQ ID NO 11
<211> LENGTH: 33
<212> TYPE: PRT
<213> ORGANISM: artificial
<220> FEATURE:
<223> OTHER INFORMATION: alphavirus non sturctural polyprotein P1234
<220> FEATURE:
<221> NAME/KEY: MISC_FEATURE
<222> LOCATION: (1)..(33)
<223> OTHER INFORMATION: 15/20 recognition site variant
<220> FEATURE:
<221> NAME/KEY: MISC_FEATURE
<222> LOCATION: (16)..(16)
<223> OTHER INFORMATION: +1 amino acid

<400> SEQUENCE:

```
<213> ORGANISM: artificial
<220> FEATURE:
<223> OTHER INFORMATION: alphavirus non structural polyprotein P1234
<220> FEATURE:
<221> NAME/KEY: MISC_FEATURE
<222> LOCATION: (1)..(34)
<223> OTHER INFORMATION: 20/15 recognition site variant
<220> FEATURE:
<221> NAME/KEY: MISC_FEATURE
<222> LOCATION: (20)..(20)
<223> OTHER INFORMATION: +1 amino acid

<400> SEQUENCE: 14

Ser Gly Ile Thr Phe Gly Asp Phe Asp Asp Val Leu Arg Leu Gly Arg
1               5                   10                  15

Ala Gly Ala Tyr Ile Phe Ser Ser Asp Thr Gly Ser Gly His Leu Gln
            20                  25                  30

Gln Lys

<210> SEQ ID NO 15
<211> LENGTH: 29
<212> TYPE: PRT
<213> ORGANISM: artificial
<220> FEATURE:
<223> OTHER INFORMATION: alphavirus non structural polyprotein P1234
<220> FEATURE:
<221> NAME/KEY: MISC_FEATURE
<222> LOCATION: (1)..(29)
<223> OTHER INFORMATION: 20/10 recognition site variant
<220> FEATURE:
<221> NAME/KEY: MISC_FEATURE
<222> LOCATION: (20)..(20)
<223> OTHER INFORMATION: +1 amino acid

<400> SEQUENCE: 15

Ser Gly Ile Thr Phe Gly Asp Phe Asp Asp Val Leu Arg Leu Gly Arg
1               5                   10                  15

Ala Gly Ala Tyr Ile Phe Ser Ser Asp Thr Gly Ser Gly
            20                  25

<210> SEQ ID NO 16
<211> LENGTH: 24
<212> TYPE: PRT
<213> ORGANISM: artificial
<220> FEATURE:
<223> OTHER INFORMATION: alphavirus non structural polyprotein P12334
<220> FEATURE:
<221> NAME/KEY: MISC_FEATURE
<222> LOCATION: (1)..(24)
<223> OTHER INFORMATION: 20/5 recognition site variant
<220> FEATURE:
<221> NAME/KEY: MISC_FEATURE
<222> LOCATION: (20)..(20)
<223> OTHER INFORMATION: +1 amino acid

<400> SEQUENCE: 16

Ser Gly Ile Thr Phe Gly Asp Phe Asp Asp Val Leu Arg Leu Gly Arg
1               5                   10                  15

Ala Gly Ala Tyr Ile Phe Ser Ser
            20

<210> SEQ ID NO 17
<211> LENGTH: 29
<212> TYPE: PRT
<213> ORGANISM: artificial
<220> FEATURE:
<223> OTHER INFORMATION: alphavirus nonstructural polyprotein P1234
<220> FEATURE:
<221> NAME/KEY: MISC_FEATURE
```

-continued

```
<222> LOCATION: (1)..(29)
<223> OTHER INFORMATION: 20/0 recoginition site variant
<220> FEATURE:
<221> NAME/KEY: MISC_FEATURE
<222> LOCATION: (19)..(19)
<223> OTHER INFORMATION: -1 amino acid
<220> FEATURE:
<221> NAME/KEY: MISC_FEATURE
<222> LOCATION: (20)..(29)
<223> OTHER INFORMATION: Histidine tag

<400> SEQUENCE: 17

Ser Gly Ile Thr Phe Gly Asp Phe Asp Asp Val Leu Arg Leu Gly Arg
1               5                   10                  15

Ala Gly Ala Leu Glu His His His His His His His His
            20                  25

<210> SEQ ID NO 18
<211> LENGTH: 14
<212> TYPE: PRT
<213> ORGANISM: artificial
<220> FEATURE:
<223> OTHER INFORMATION: alphavirus nonstructural polyprotein P1234
<220> FEATURE:
<221> NAME/KEY: MISC_FEATURE
<222> LOCATION: (1)..(14)
<223> OTHER INFORMATION: 9/5 recognition site variant
<220> FEATURE:
<221> NAME/KEY: MISC_FEATURE
<222> LOCATION: (10)..(14)
<223> OTHER INFORMATION: +1 amino acid

<400> SEQUENCE: 18

Val Leu Arg Leu Gly Arg Ala Gly Ala Tyr Ile Phe Ser Ser
1               5                   10

<210> SEQ ID NO 19
<211> LENGTH: 13
<212> TYPE: PRT
<213> ORGANISM: artificial
<220> FEATURE:
<223> OTHER INFORMATION: alohavirus nonstructural polyprotein P1234
<220> FEATURE:
<221> NAME/KEY: MISC_FEATURE
<222> LOCATION: (1)..(13)
<223> OTHER INFORMATION: 8/5 recoginiton site variant
<220> FEATURE:
<221> NAME/KEY: MISC_FEATURE
<222> LOCATION: (9)..(9)
<223> OTHER INFORMATION: +1 amino acid

<400> SEQUENCE: 19

Leu Arg Leu Gly Arg Ala Gly Ala Tyr Ile Phe Ser Ser
1               5                   10

<210> SEQ ID NO 20
<211> LENGTH: 12
<212> TYPE: PRT
<213> ORGANISM: artificial
<220> FEATURE:
<223> OTHER INFORMATION: alphavirus non structural polyprotein P1234
<220> FEATURE:
<221> NAME/KEY: MISC_FEATURE
<222> LOCATION: (1)..(12)
<223> OTHER INFORMATION: 7/5 recognition site variant
<220> FEATURE:
<221> NAME/KEY: MISC_FEATURE
<222> LOCATION: (8)..(8)
<223> OTHER INFORMATION: +1 amino acid

<400> SEQUENCE: 20
```

```
Arg Leu Gly Arg Ala Gly Ala Tyr Ile Phe Ser Ser
1               5                   10
```

```
<210> SEQ ID NO 21
<211> LENGTH: 10
<212> TYPE: PRT
<213> ORGANISM: artificial
<220> FEATURE:
<223> OTHER INFORMATION: alphavirus nonstructural polyprotein P1234
<220> FEATURE:
<221> NAME/KEY: MISC_FEATURE
<222> LOCATION: (1)..(10)
<223> OTHER INFORMATION: 5/5 recognition site variant
<220> FEATURE:
<221> NAME/KEY: MISC_FEATURE
<222> LOCATION: (6)..(6)
<223> OTHER INFORMATION: +1 amino acid

<400> SEQUENCE: 21

Gly Arg Ala Gly Ala Tyr Ile Phe Ser Ser
1               5                   10
```

```
<210> SEQ ID NO 22
<211> LENGTH: 16
<212> TYPE: PRT
<213> ORGANISM: artificial
<220> FEATURE:
<223> OTHER INFORMATION: alphavirus non structural polyprotein P1234
<220> FEATURE:
<221> NAME/KEY: MISC_FEATURE
<222> LOCATION: (1)..(16)
<223> OTHER INFORMATION: 15/Y rec

```
<222> LOCATION: (16)..(16)
<223> OTHER INFORMATION: +1 amino acid

<400> SEQUENCE: 24

Phe Gly Asp Phe Asp Asp Val Leu Arg Leu Gly Arg Ala Gly Ala Gly
1               5                   10                  15

<210> SEQ ID NO 25
<211> LENGTH: 16
<212> TYPE: PRT
<213> ORGANISM: artificial
<220> FEATURE:
<223> OTHER INFORMATION: alphavirus non structural polyprotein P1234
<220> FEATURE:
<221> NAME/KEY: MISC_FEATURE
<222> LOCATION: (1)..(16)
<223> OTHER INFORMATION: 15/R recognition site variant
<220> FEATURE:
<221> NAME/KEY: MISC_FEATURE
<222> LOCATION: (16)..(16)
<223> OTHER INFORMATION: +1 amino acid

<400> SEQUENCE: 25

Phe Gly Asp Phe Asp Asp Val Leu Arg Leu Gly Arg Ala Gly Ala Arg
1               5                   10                  15

<210> SEQ ID NO 26
<211> LENGTH: 16
<212> TYPE: PRT
<213> ORGANISM: artificial
<220> FEATURE:
<223> OTHER INFORMATION: alphavirus non structural polyprotein P1234
<220> FEATURE:
<221> NAME/KEY: MISC_FEATURE
<222> LOCATION: (1)..(16)
<223> OTHER INFORMATION: 15/S recognition site variant
<220> FEATURE:
<221> NAME/KEY: MISC_FEATURE
<222> LOCATION: (16)..(16)
<223> OTHER INFORMATION: +1 amino acid

<400> SEQUENCE: 26

Phe Gly Asp Phe Asp Asp Val Leu Arg Leu Gly Arg Ala Gly Ala Ser
1               5                   10                  15

<210> SEQ ID NO 27
<211> LENGTH: 16
<212> TYPE: PRT
<213> ORGANISM: artificial
<220> FEATURE:
<223> OTHER INFORMATION: alphavirus non structural polyprotein P1234
<220> FEATURE:
<221> NAME/KEY: MISC_FEATURE
<222> LOCATION: (1)..(16)
<223> OTHER INFORMATION: 15/N recognition site variant
<220> FEATURE:
<221> NAME/KEY: MISC_FEATURE
<222> LOCATION: (16)..(16)
<223> OTHER INFORMATION: +1 amino acid

<400> SEQUENCE: 27

Phe Gly Asp Phe Asp Asp Val Leu Arg Leu Gly Arg Ala Gly Ala Asn
1               5                   10                  15

<210> SEQ ID NO 28
<211> LENGTH: 16
<212> TYPE: PRT
<213> ORGANISM: artificial
<220> FEATURE:
<223> OTHER INFORMATION: alphavirus nonstructural polyprotein P1234
<220> FEATURE:

```
<221> NAME/KEY: MISC_FEATURE
<222> LOCATION: (1)..(16)
<223> OTHER INFORMATION: 15/E recognition site variant
<220> FEATURE:
<221> NAME/KEY: MISC_FEATURE
<222> LOCATION: (16)..(16)
<223> OTHER INFORMATION: +1 amino acid

<400> SEQUENCE: 28

Phe Gly Asp Phe Asp Asp Val Leu Arg Leu Gly Arg Ala Gly Ala Glu
1               5                   10                  15

<210> SEQ ID NO 29
<211> LENGTH: 16
<212> TYPE: PRT
<213> ORGANISM: artificial
<220> FEATURE:
<223> OTHER INFORMATION: alphavirus non structural polyprotein P1234
<220> FEATURE:
<221> NAME/KEY: MISC_FEATURE
<222> LOCATION: (1)..(16)
<223> OTHER INFORMATION: 15/D srecognition site variant
<220> FEATURE:
<221> NAME/KEY: MISC_FEATURE
<222> LOCATION: (16)..(16)
<223> OTHER INFORMATION: +1 amino acid

<400> SEQUENCE: 29

Phe Gly Asp Phe Asp Asp Val Leu Arg Leu Gly Arg Ala Gly Ala Asp
1               5                   10                  15

<210> SEQ ID NO 30
<211> LENGTH: 11
<212> TYPE: PRT
<213> ORGANISM: artificial
<220> FEATURE:
<223> OTHER INFORMATION: alphavirus nonstructural polyprotein P1234
<220> FEATURE:
<221> NAME/KEY: MISC_FEATURE
<222> LOCATION: (1)..(11)
<223> OTHER INFORMATION: 10/S recognition site variant
<220> FEATURE:
<221> NAME/KEY: MISC_FEATURE
<222> LOCATION: (11)..(11)
<223> OTHER INFORMATION: +1 amino acid

<400> SEQUENCE: 30

Asp Val Leu Arg Leu Gly Arg Ala Gly Ala Ser
1               5                   10

<210> SEQ ID NO 31
<211> LENGTH: 7
<212> TYPE: PRT
<213> ORGANISM: artificial
<220> FEATURE:
<223> OTHER INFORMATION: alphavirus nonstructural polyprotein P1234
<220> FEATURE:
<221> NAME/KEY: MISC_FEATURE
<222> LOCATION: (1)..(7)
<223> OTHER INFORMATION: 6/S recognition site variant
<220> FEATURE:
<221> NAME/KEY: MISC_FEATURE
<222> LOCATION: (7)..(7)
<223> OTHER INFORMATION: +1 amino acid

<400> SEQUENCE: 31

Leu Gly Arg Ala Gly Ala Ser
1               5

<210> SEQ ID NO 32
<211> LENGTH: 11
```

```
<212> TYPE: PRT
<213> ORGANISM: artificial
<220> FEATURE:
<223> OTHER INFORMATION: alphavirus nonstructural polyprotein P1234
<220> FEATURE:
<221> NAME/KEY: MISC_FEATURE
<222> LOCATION: (1)..(11)
<223> OTHER INFORMATION: 16/S5 recognition site variant
<220> FEATURE:
<221> NAME/KEY: MISC_FEATURE
<222> LOCATION: (7)..(7)
<223> OTHER INFORMATION: +1 amino acid
<220> FEATURE:
<221> NAME/KEY: MISC_FEATURE
<222> LOCATION: (11)..(11)
<223> OTHER INFORMATION: +1 amino acid

<400> SEQUENCE: 32

Leu Gly Arg Ala Gly Ala Ser Ile Phe Ser Ser
1               5                   10

<210> SEQ ID NO 33
<211> LENGTH: 15
<212> TYPE: PRT
<213> ORGANISM: artificial
<220> FEATURE:
<223> OTHER INFORMATION: alphavirus nonstructural polyprotein P1234
<220> FEATURE:
<221> NAME/KEY: MISC_FEATURE
<222> LOCATION: (1)..(15)
<223> OTHER INFORMATION: 10/S5 recognition site variant
<220> FEATURE:
<221> NAME/KEY: MISC_FEATURE
<222> LOCATION: (7)..(7)
<223> OTHER INFORMATION: +1 amino acid
<220> FEATURE:
<221> NAME/KEY: MISC_FEATURE
<222> LOCATION: (11)..(11)
<223> OTHER INFORMATION: +1 amino acid

<400> SEQUENCE: 33

Asp Val Leu Arg Leu Gly Arg Ala Gly Ala Ser Ile Phe Ser Ser
1               5                   10                  15
```

OPTIMIZED RECOGNITION SITE OF THE ALPHAVIRUS NON-STRUCTURAL PROTEASE FOR TAG REMOVAL AND SPECIFIC PROCESSING OF RECOMBINANT PROTEINS

PRIORITY

This application claims priority of the U.S. Provisional patent application number 60/581,579 filed on Jun. 21, 2004.

SEQUENCE LISTING

This application contains sequence data provided on a computer readable diskette and as a paper version. The paper version of the sequence data is identical to the data provided on the diskette.

BACKGROUND OF THE INVENTION

1. Technical Field of the Invention

The present invention relates to protein detection and purification. More specifically the invention relates to protein recognition sites. Even more specifically the invention relates to the modified peptide sequence from the Semliki Forest Virus (SFV) encoded non-structural protein suitable for use as recognition site for recombinant non-structural protease of SFV (hereafter "SFV protease site"), the nucleotide sequence and its variants that encode the recognition site. The invention also extends to the SFV protease recognition site fused into a polypeptide, inserted into a polypeptide sequence or placed between any peptide or protein tag and polypeptide sequence. The invention also extends to the methods for using the SFV protease site and corresponding enzyme.

2. Background of the Invention

Site-specific proteolytic processing of expressed proteins is a widely used technical approach. This approach is used to remove unwanted sequences from expressed and purified recombinant proteins. Such unwanted sequences are often expression and/or purification tags; they can be peptide tags or protein tags. Peptide tags usually contain 4 to 20 amino acids, while protein tags usually have a molecule weight of some kDas. This approach is also used to process the multi-domain proteins into individual proteins both in vitro and in vivo (in living cells) conditions. Currently this approach is commonly used, but along with development of the methods of functional proteomics and methods for analysis of protein-protein interactions and protein functions directly in cell there is an increasing need for more precise, highly specific effective instruments.

Tagging (epitope tags, affinity tags, tags which stabilize the expressed protein or facilitate its correct folding in cells) is a widely used technology. Most of the proteins, currently used in biotechnology industry and for research purposes, are at some stage expressed as tagged fusion proteins since this allows using common and well established technologies for their detection, purification and concentration. However, because tags are usually immunogenic; because they can affect the protein structure and its ability to crystallize; because they can also mask the functional domains of recombinant protein and/or block specific and significant interactions with other proteins or cofactors, removal of the tags is an essential step before functional characterization of these recombinant proteins is possible. The tag removal is usually achieved by use of site specific processing with different proteases (thrombin, enterokinase, factor Xa, TEV (tobacco etch virus) protease and several others). Tag removal with proteases requires that the sequence encoding for protease recognition site has to be included in the expression vector. This sets certain limitations for protease recognition sites that can be used for this kind of vector type design:

sites should be relatively short;
sites should be cleaved only by specific protease;
sites should be cleaved with efficiency close to 100%.

Since all these properties can not always be combined inside of one vector, one usually has to choose between different sets of vectors depending on the purposes: Vectors with maximally efficient cleavage site provide rapid and highly efficient cleavage. With this kind of cleavage sites in the vector the amount of substrate processed by one unit of enzyme is as high as possible. Vectors with maximally precise cleavage site provide cleavage to take place as close as possible to the N- or C-terminus of recombinant proteins. Thus, depending on the nature of experimental and/or technological setup using one and same enzyme different cleavage sites can provide different results.

For use of the cleavage in in vivo conditions additional requirements will apply. The protease used for these experiments must be highly specific, must not cause injuries of the cells and the cleavage should be highly efficient. One application of the in vivo cleavage is to affect on the expression protein stability by removing degradation signals from the protein or to cleave protein in such a way that the N-terminal amino acid residue of cleaved protein will be recognized by protein degradation machinery and the cleaved protein will be degraded by N-end rule. For this kind of approach either inducible cell lines, conditionally expressing the protease or high efficiency cell co-transfection systems would be beneficial.

The high importance of these problems has led to commercialization of set of enzymes with site specific protease activity and corresponding vector plasmids. The enzymes have different (cellular, viral) origins and include thrombin, enterokinase, factor Xa, TEV (tobacco etch virus) protease and several others. The list of enzymes used for these purposes is growing and the information of the enzymatic and structural properties is expanding. The ideal combination of protease and its recognition sequence should fulfill the following criteria:

high efficiency at wide diapason of conditions (temperature, ionic condition, pH);
high specificity for cleavage consensus, no secondary cleavages or side effects;
possibility to make cleavages precisely at the end (N- and/or C-terminus) of recombinant protein;
possibility to perform the reaction in vivo and in vitro;
existence of easy to use and reversible inhibitors of protease activity.

In spite of the efforts to develop an ideal combination, so far none of the available protease/recognition site-combinations meets all the conditions of an ideal system as listed above. The present invention discloses a system that meets all these conditions and thereby introduces a novel, highly useful, precise and specific tool for site-specific proteolytic processing of proteins.

Semliki Forest virus (SFV) belongs to genus *Alphavirus* (family Togaviridae) together with 27 other known viruses. Alpha viruses infect their vertebrate hosts (mammals, birds and fish) and invertebrate transmission vectors (mosquitoes). In infected organisms the alpha viruses replicate in different cells to a high titer.

Alphavirus genome encodes for two protease activities—one is associated with virus coat protein which is an autoproteinase and another with non-structural protein nsP2, which cleaves three cleavage sites in alpha virus nonstructural polyprotein P1234 (Merits et al., 2001, J. Gen Virol. 2001: 82:765–773). These cleavage sites have different consensus sequences and they differ from each other by the mode of proteolytic cleavage (in cis or in trans), the enzymatic activity required for the cleavage (intact nsP2 or protease domain of nsP2) and by the cleavage efficiency (Vasilieva et al., 2001: J. of Biol. Chem. 276(33): 30786–30793).

NsP2 consists of two enzymatically active domains: N-terminal NTPase/helicase/RNA triphosphatase domain and C-terminal cystein protease domain. Both domains are needed for virus replication and for processing of the second cleavage site in SFV polyprotein, while only the C-terminal protease domain is needed for processing the third cleavage site (between nsP3 and nsP4). Cysteine 481 and histidine 558 have been identified as essential residues for the protease activity of nsP2. It has been shown that nsP2 protease domain (hereafter named Pro39 ) can be expressed as recombinant protein in E. coli, purified with Ni-NTA chromatography and used for in vitro processing of the recombinant substrates, containing 37 aa region of the protease recognition site (19 aa residues upstream and 18 aa residues downstream of the cleavage point; hereafter 19/18 recognition site). (Vasiljeva et al. 2001). The cleavage is highly specific and active; Pro39 is capable to process 50% of 400-fold molar excess of substrate in 5 minutes. (Vasilieva et al., 2001). FIG. 1 illustrates the structure and processing pattern of SFV nonstructural polyprotein.

One of the biological functions of cleavage of the protease site between nsP3 and nsP4 proteins is to release the nsP4 from P1234 precursor protein and from alpha virus early replicase complex. SFV, in contrast to majority of alpha viruses analyzed to the date produces atypically large amounts of P1234 polyprotein; in case of most other alpha viruses the P1234 production is about 20 fold down-regulated by presence of leaky termination codon at the end of nsP3 region. This leads us to believe that compared to most alpha virus proteases the SFV nsP2 protease should have a higher cleavage activity for the last processing site, since it has to digest significantly higher amounts of substrate. It may also be that proteases from other alpha viruses may have similar high activities.

SUMMARY OF THE INVENTION

The present invention relates to linear protease recognition site from the SFV encoded polyprotein which in truncated and modified forms can be used as highly efficient and precise target sequence for the SFV non-structural protease nsP2 and for its C-terminal protease domain Pro39 . The target sequence has earlier been identified as a 37 aa long sequence which however, is far too large for use in any practical expression system. On the contrary, the present disclosure provides a target sequence that can easily be used in various expression systems.

The present disclosure provides details of the protease recognition site requirements. This disclosure shows that the target sequence of Pro39 can surprisingly be truncated into shorter but still very efficiently cleavable variants. The cleavage efficiency for the artificial protease substrates containing these sequences is somewhat lower than the efficiency of full-size 19/18 recognition site, but unexpectedly it is high enough to enable protease to process over 10-fold molar excesses of substrate within one hour. According to the present disclosure the cleavage specificity was also maintained for these truncated sites. The preferred sequences according to the present disclosure for active recognition site variants are:

```
1. (-10)DVLRLGRAGA(↓)YIFSS (+5),    (SEQ ID NO:1)
   designated as 10/5 site 2. (-6)LGRAGA(↓)YIFSS (+5);         (SEQ ID NO:2)
   designated as 6/5 site.
```

Moreover, the present disclosure shows that the +1 amino acid residue of the protease recognition site can be substituted from native Y (tyrosine) to virtually any type of amino acid with no change of protease cleavage specificity. If the native Y residue is substituted with S (serine) and R (arginine) residues the cleavage site recognition and/or processing efficiency is significantly enhanced. G (glycine) was found to be the best residue to substitute native Y residue as the substrate containing G was processed 3 fold more effectively as compared to native Y containing substrate. Substrates with R and S residues are processed 2 fold more efficiently as compared to substrates with native Y in the same position.

Even further, the present disclosure shows that the protease recognition downstream region can be substituted with His-tag repeat. Such substitution does not affect the cleavage as such but only the efficiency of the cleavage.

In one aspect of the invention these inventive steps are successfully combined. It is demonstrated that artificial truncated substrates with altered +1 amino acid residues are efficiently recognized and actively processed by Pro39 , the processing is more rapid and complete as compared to substrates where it truncated sites are used. Preferred embodiments of the present invention therefore include the following variants of the highly effective protease recognition sites:

```
3. (-10)DVLRLGRAGA(↓)RIFSS (+5),    (SEQ ID NO:3)
   designated as 10/R5 site 4. (-6)LGRAGA(↓)RIFSS (+5);         (SEQ ID NO:4)
   designated as 6/R5 site 5. (-10)DVLRLGRAGA(↓)GIFSS (+5),    (SEQ ID NO:5)
   designated as 10/G5 site 6. (-6)LGRAGA(↓)GIFSS (+5);         (SEQ ID NO:6)
   designated as 6/G5 site 7. (-6)LGRAGA(↓)SIFSS (+5);         (SEQ ID NO:32)
   designated as 6/S5 site 8. (-10)DVLRLGRAGA(↓)SIFSS (+5),    (SEQ ID NO:33)
   designated as 10/S5 site
```

Importantly, cleavage specificity is preserved for all of these modified recognition sites.

In another aspect of this invention the ability of Pro39 to process differently positioned modified recognition sites in recombinant target protein was examined. Positioning the recognition sequence between highly structured thioredoxine domains does surprisingly not cause decrease of protease cleavage efficiency, but on the contrary, the cleavage efficiency is significantly enhanced as compared to cleavage of recognition sites placed between structured and non-structured protein sequences.

According to the present disclosure Pro39 cleaves substrates possessing the truncated and modified recognition site in wide temperature range (including low temperatures) 4–39° C., in neutral pH region (i.e. pH 7–8) and in presence of high concentration NaCl (up to 4 M) or urea (up to 1.5 M).

Furthermore, according to the present disclosure the cleavage of the substrates possessing the truncated and modified recognition sites can be reversibly inhibited by addition of Zn-ions and re-activated by addition of EDTA. Furthermore, Pro39 cleaves substrates having the recognition site according to this disclosure both in liquid phase as well as in resin-bound state.

One object of the present invention is to use modified recognition sites for Pro39 for removal of large and structured protein tags such as thioredoxine, GST (glutathione S-transferase), MBP (maltose binding protein) or CBP (calmoduline binding protein) from recombinant proteins.

Another object of the present invention is to insert the modified recognition site(s) for Pro39 into recombinant protein sequence and the recombinant protein can subsequently be processed into subdomains with desired sizes.

A still another object of the present invention is to provide a cleavage site and a protease that can be used in wide temperature range, at neutral pH, and under high salt concentration. Moreover, an object of the present invention is to provide a cleavage site and protease that can be used as well in liquid phase as in a resin bound stage.

An even further aspect of the present invention is to provide expression vectors comprising sequences encoding recombinant proteins and modified recognition sites for Pro39 to subsequently process the protein

A. Effect of temperature. Purified substrate was incubated with Pro39 for 60 minutes in molar ratio 20:1 at temperature indicated on the top of each lane. Reaction products were analyzed by SDS-PAGE and visualized by Coomassie Blue staining. Lane 1 contains the same substrate with no Pro39 added. Positions of Pro39, substrates and cleavage products are indicated on the right hand side of the blot.

B. Effect of pH. Purified substrate was incubated with Pro39 for 60 minutes at 30° C. in molar ration 20:1 in HEPES buffer with pH indicated at the top of each lane. Reaction products were analyzed by SDS-PAGE and visualized by Coomassie staining. Positions of Pro39, substrates and cleavage products are indicated on the right hand side of the blot.

Figure 8A:
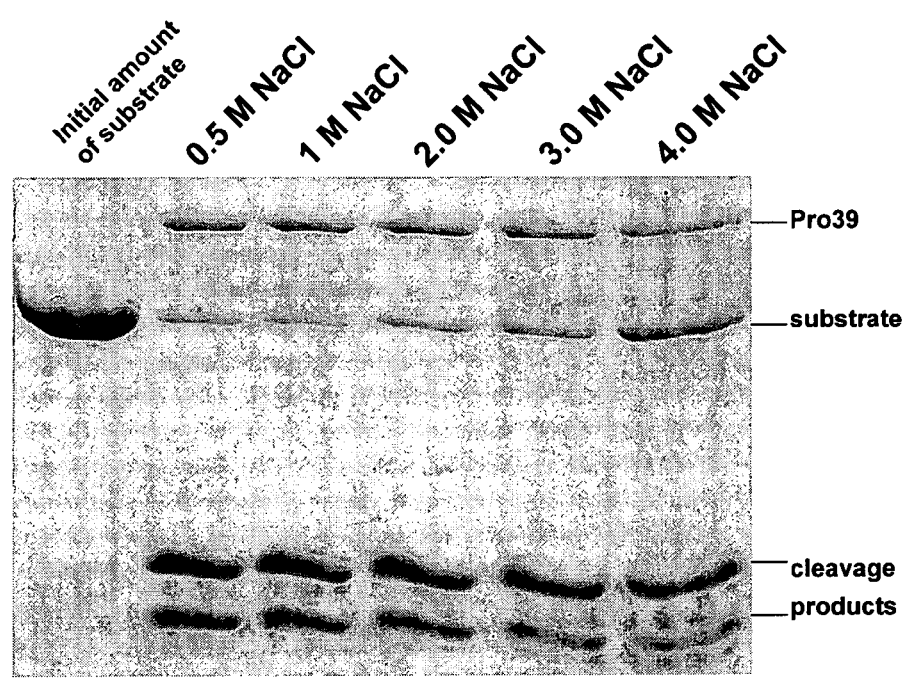
Figure 8B:
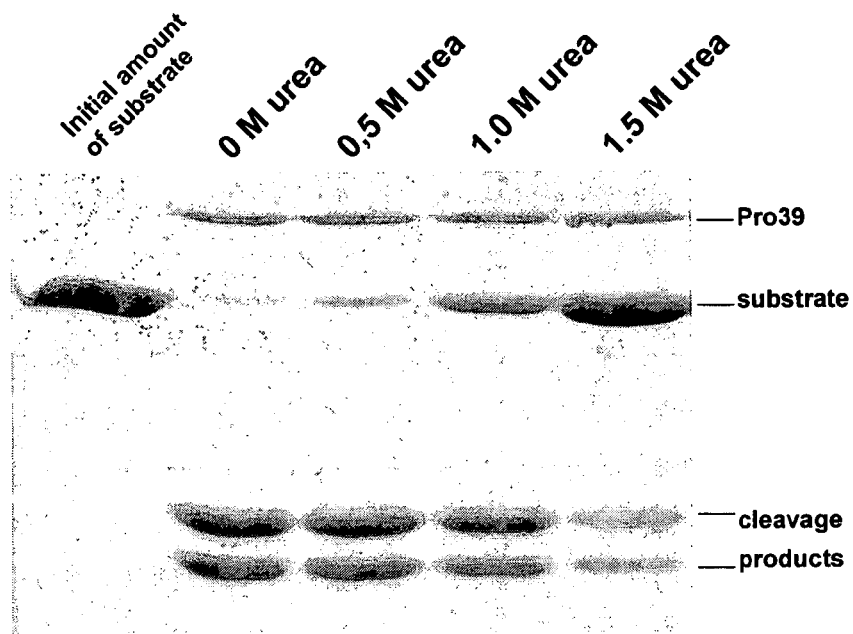

FIG. 8 illustrates the effects of cleavage conditions for processing of the modified recognition sites by Pro39. The substrate used in this experiment was Trx fused with 10/5 recognition site.

A. Activity of Pro39 in presence of high molar salt. Purified substrate was incubated with Pro 39 for 60 minutes at 30° C. in molar ration 20:1 in presence of NaCl concentrations indicated at the top of each Lane. Reaction products were analyzed by SDS-PAGE and visualized by Coomassie Blue staining. Lane 1 contains the same substrate with no Pro39 added. Positions of Pro39, substrates and cleavage products are indicated on the right hand side of the blot.

B. Activity of Pro39 in presence of urea. Purified substrate was incubated with Pro39 for 60 minutes at 30° C. in molar ration 20:1 at presence of urea concentrations indicated at the top of each lane. Reaction products were analyzed by SDS-PAGE and visualized by Coomassie Blue staining. Lane 1 contains the same substrate with no Pro39 added. Positions of Pro39, substrates and cleavage products are indicated on the right hand side of the blot FIG. 9 demonstrates the reversible inhibition of Pro39 at the presence of zinc ions. Purified substrate was incubated with Pro39 at 30° C. in molar ration 20:1. Lane 1 (control) contains substrate with no Pro39 added. Lane 2 represents the products of reaction after 10 minutes of incubation. Lane 3 represents the products of reaction incubated for 10 minutes, stopped by addition of zinc ions and incubated for an additional 60 minutes. Lane 4 represent the products of reaction incubated for 10 minutes, stopped by addition of zing, reactivated by addition of EDTA and incubated for an additional 60 minutes. Lane 5 represents the products of reaction after 60 minutes of incubation with no zinc addition. Position of Pro39, substrates and cleavage products are indicated on the right hand side of the blot.

Figure 10:

FIG. 10A shows the schematic structure of TAP-DBD substrate used to demonstrate Pro39 cleavage of substrate purified on anti-E2Tag antibody conjugated Sepharose resin. E2Tag indicates sequence SSTSSDFRDR (SEQ ID NO: 7) recognized by anit-E2Tag antibody 5El 1, E4Tag indicates sequence GTTGHYSVRD (SEQ ID NO: 8) recognized by anti-E4Tag antibody 1E2, DBD represents BPV-1E2 protein DNA Binding and Dimerization domain. Arrow indicates the position of Pro39 cleavage.

Figure 10B:

FIG. 10B demonstrates Pro39 cleavage of substrate purified on anti-E2Tag antibody conjugated Sepharose resin. Purified substrate TAP-DBD as illustrated in FIG. 10A was incubated with Pro39 at 30° C. for times indicated at the top of each lane. Reaction products were analyzed by Western Blot method using anti-E4Tag antibody 1E2 and goat anti-mouse IgG alkaline phosphatase conjugate as secondary antibody. Signals visualized using bromochloroindoyl phosphate/nitro blue tetrazolium (BCIP/NBT). Lane 1 represents non purified substrate (TAP-DBD lysate). Lane 2 represents the products of reaction after 2 hours incubation. Lane 3 represents the products of reaction after 4 hours incubation. Positions of substrate and cleavage products are indicated on the right hand side of the blot.

Figure 11A:

FIG. 11A shows a schematic structure of HisTag-EGFP-HisTag substrate used to demonstrate effect of low incubation temperature on the Pro39 cleavage activity.

FIG. 11B demonstrates activity of Pro39 on the recombinant substrate under low temperature conditions. Purified substrate (E2Tag-HisTag-EGFP-HisTag as illustrated in FIG. 11A, was incubated with Pro39 in molar ratio 10:1 at 8C for times indicated on top of each lane. Reaction products were analyzed by Western Blot method using anti-His antibody and goat anti-mouse IgG alkaline phosphatase conjugate as secondary antibody. Signals were visualized using bromoclhoroindolyl phosphate/nitro blue tetrazolium (BCIP/NBT). Lane 1 represents the products of reaction after 23 hours incubation. Lane 2 represents the products of reaction after 6 hours incubation. Lane 3 represents the products of reaction after 9 hours incubation. Lane 4 resents the products of reaction after 21 hours incubation. Lane 5 represents non treated substrate and Pro39 as molecular weight markers. Positions of Pro39, substrate and cleavage products are indicated on the left hand side of the blot.

Figure 12:
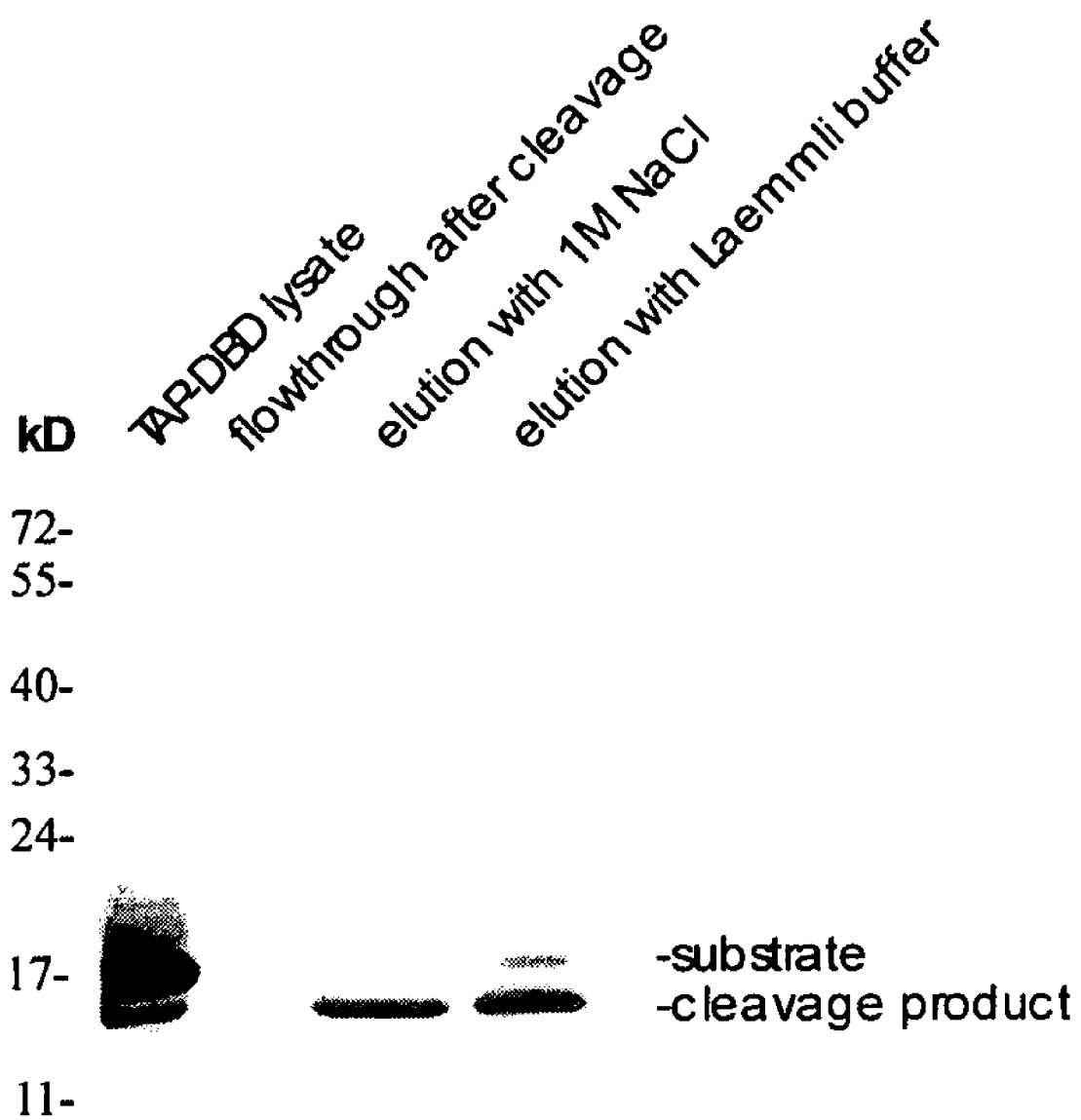

FIG. 12 demonstrates cleavage of column-bound substrate TAP-DBD (illustrated in FIG. 10A) by Pro 39 on column. Reaction products were analyzed by Western Blot method using anti-E4Tag antibody 1E2. Goat anti-mouse IgG alkaline phosphatase conjugate was used as secondary antibody. Signals were visualized using bromoclhoroindolyl phosphate/nitro blue tetrazolium (BCIP/NBT). Lane 1 represents total cell lysate. Lane 2 represents flow through fraction after Pro39 cleavage. Lane 3 represents elution of cleavage product. Lane 4 represents column-bound fraction (uncleaved substrate and cleavage products) after Pro39 cleavage and elution. Positions of substrate and cleavage products are indicated on the right hand side of the blot.

Figure 13:
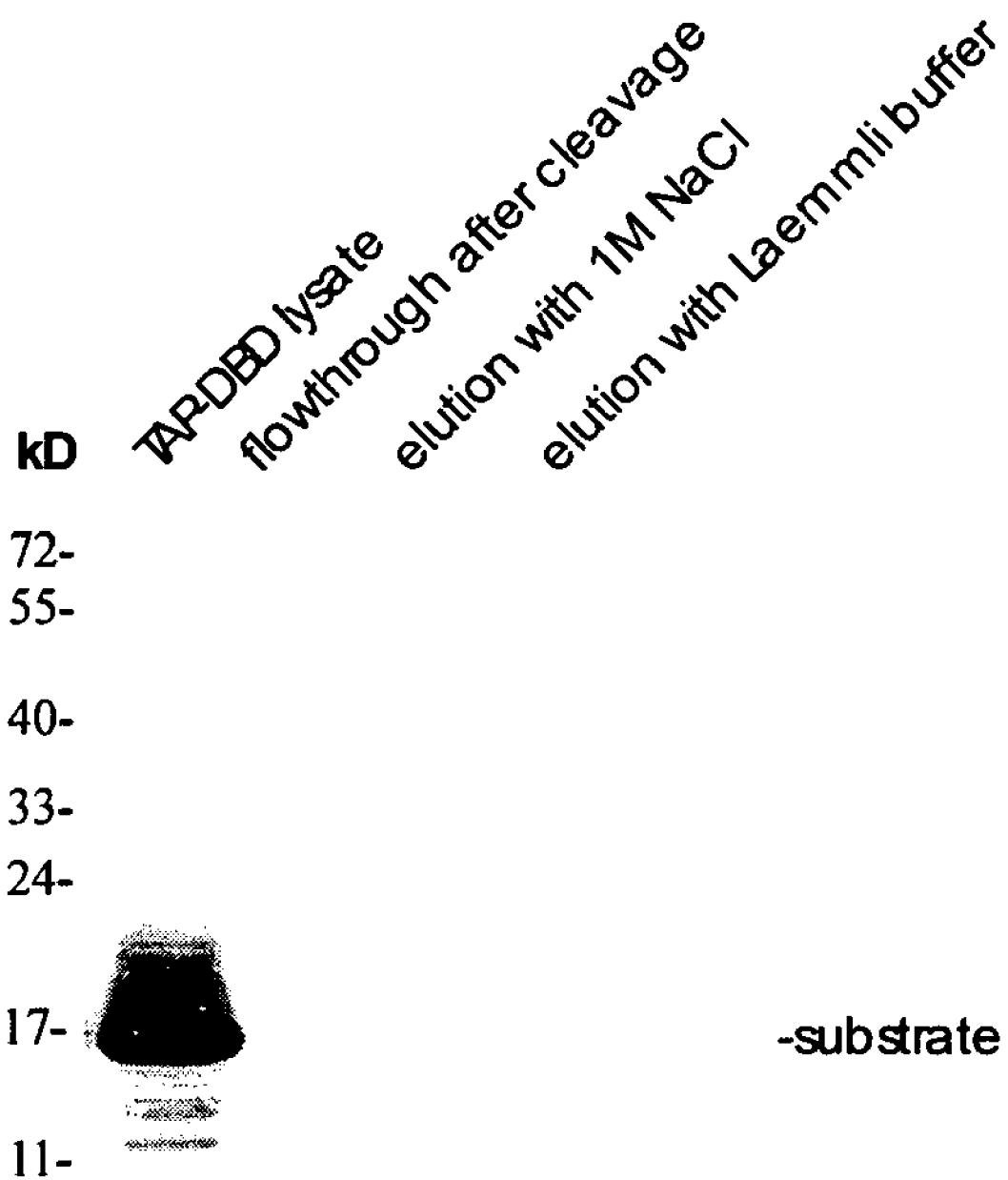

FIG. 13 demonstrates cleavage of column-bound substrate TAP-DBD (illustrated in FIG. 10A) by Pro39 on column. Reaction products were analyzed by Western blot method using anti-E2Tag antibody 5E11. Goat anti-mouse IgG alkaline phosphatase conjugate was used as secondary antibody. Signals were visualized using bromoclhoroindolyl phosphate/nitro blue tetrazolium (BCIP/NBT). Lane 1 represents total cell lysate. Lane 2 represents flow through fraction after Pro39 cleavage. Lane 3 represents elution of cleavage product. Lane 4 represents column-bound fraction after Pro39 cleavage and elution. The positions of substrate and cleavage product are indicated on the right hand side of the blot.

Figure 14:
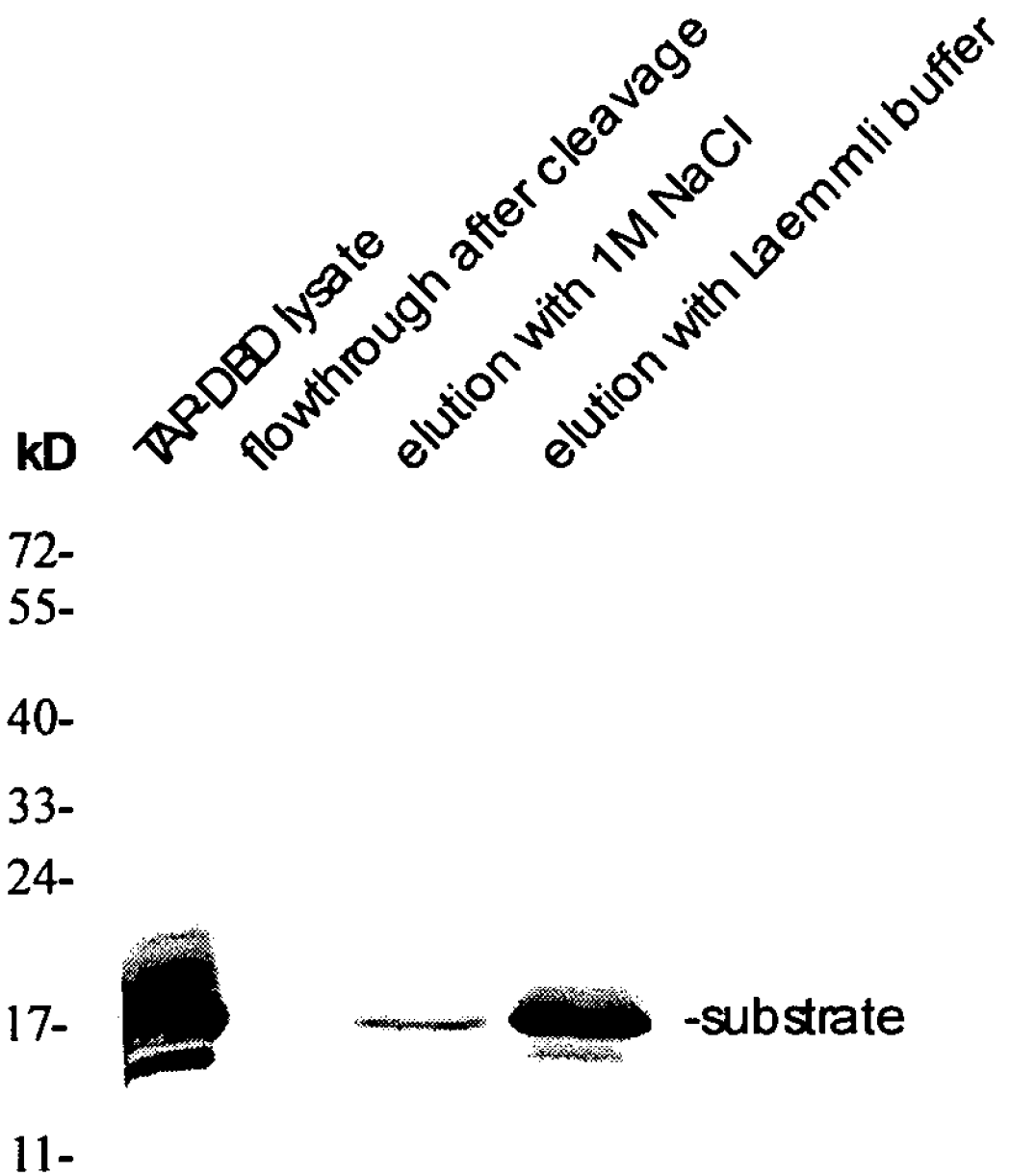

FIG. 14 demonstrates that column-bound substrate TAP-DBD (illustrated in FIG. 10A) is not cleaved without Pro39. In this control experiment anti-E2Tag antibody conjugated Sepharose resin bound substrate was incubated without Pro39 in buffer under the same conditions as with Pro39. Reaction products were analyzed by Western Blot method using anti-ETag antibody 1E2. Goat anti-mouse IgG alkaline phophatase conjugate was used as secondary antibody. Signals were visualized using bromoclhoroindolyl phosphate/nitro blue tetrazolium (BCIP/NBT). Lane 1 represents total cell lysate. Lane 2 represents flow through fraction after Pro39 cleavage. Lane 3 represents elution of cleavage products. Lane 4 represents column-bound fraction after Pro39 cleavage and elution. Position of substrate is indicated on the right hand side of the blot.

Figure 15:
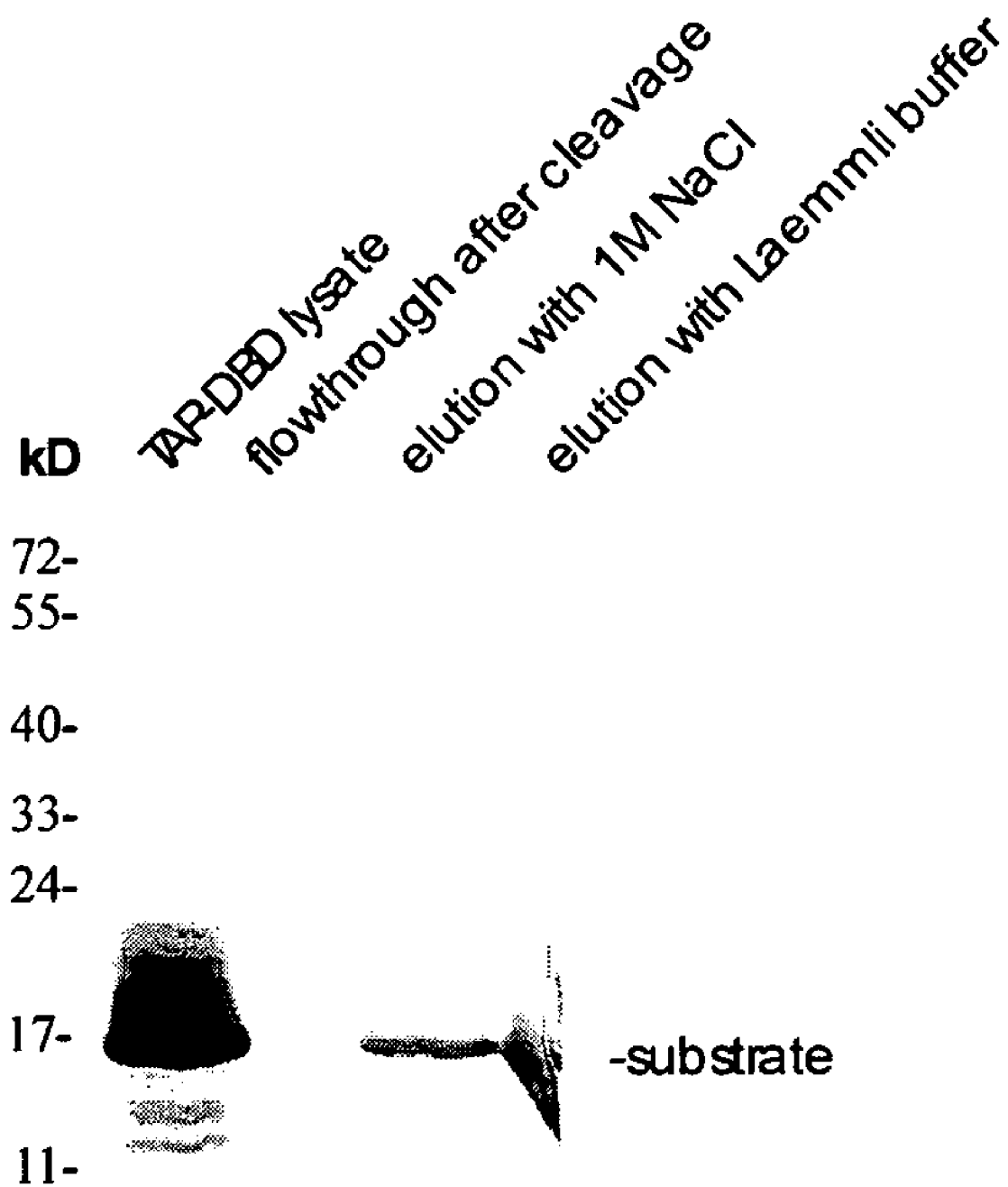

FIG. 15 demonstrates that column bound substrate TAP-DBD (illustrated in FIG. 10A) is not cleaved without Pro39. In this control experiment anti-E2Tag antibody conjugated Sepharose resin bound substrate was incubated without Pro39 in buffer under the same conditions as with Pro39. Reaction products were analyzed by Western Blot method using anti-E2Tag antibody 5E11. Goat anti-mouse IgG alkaline phosphatase conjugate was used as secondary antibody. Signals were visualized using bromoclhoroindolyl phosphate/nitro blue tetrazolium (BCIP/NBT). Lane 1 represents total cell lysate. Lane 2 represents flow through reaction after Pro39 cleavage. Lane 3 represents elution of cleavage products. Lane 4 represents column-bound fraction after Pro39 cleavage and elution. Positions of substrate and cleavage of the product are shown on the right hand side of the blot.

FIG. 16 shows the design of a vector for purposes of expression of recombinant proteins in mammalian cells. The vector is based on vector pQM-CMV-E2-N-A-intron (Quatromed Ltd. catalog number P1-114-020) Underlined sequences indicate cloning adapters for Bam HI and HindIII sites. Dotted underlined sequences indicate 6×His-tag encoding sequence. Double underlined sequences indicate cleavage site for Pdi1 (NaeI).

FIG. 17 shows the design of a vector for purposes of expression of recombinant proteins in mammalian cells. The vector is based on vector pQM-CMV-E2-N-A-intron (Quattromed Ltd. catalog number P1-114-020). Underlined sequences indicate cloning adapters for Bam HI and Hind III sites. Dotted underlined sequences indicate 6× His-tag encoding sequence. Double underlined sequences indicate CGC codon for R (Arginine) activates the cleavage of recombinant protein.

FIG. 18 depicts the full sequence of pQM-CMV-E2Tag-N-A-intron vector. The vector is of 5055 bps. Nucleotides 1–444 are for PolyA tail, 444–644 for SV40Ori, 2503–1643 for Amp, 3584–4189 for CMV, 4190–4259 for the leader, 4275–4304 E2Tag, 4304–4336 for Multiple Cloning Site and 4336–5055 intron.

DETAILED DESCRIPTION OF THE INVENTION

The present invention is related to linear protease recognition site from the SFV encoded polyprotein P1234 which, in truncated and modified forms can be used as highly efficient and precise target sequence for the SFV non-structural protease nsP2 and for its C-terminal protease domain Pro39 . In contrast to the previously identified target sequence, which is 37 aa long, and as such far too large to be used in practical expression systems, this disclosure provides shortened and still active variants as well as minimal, but still recognizable and cleavable forms of the recognition site. Additionally, this disclosure provides highly efficient modifications of the recognition site.

Figure 1:
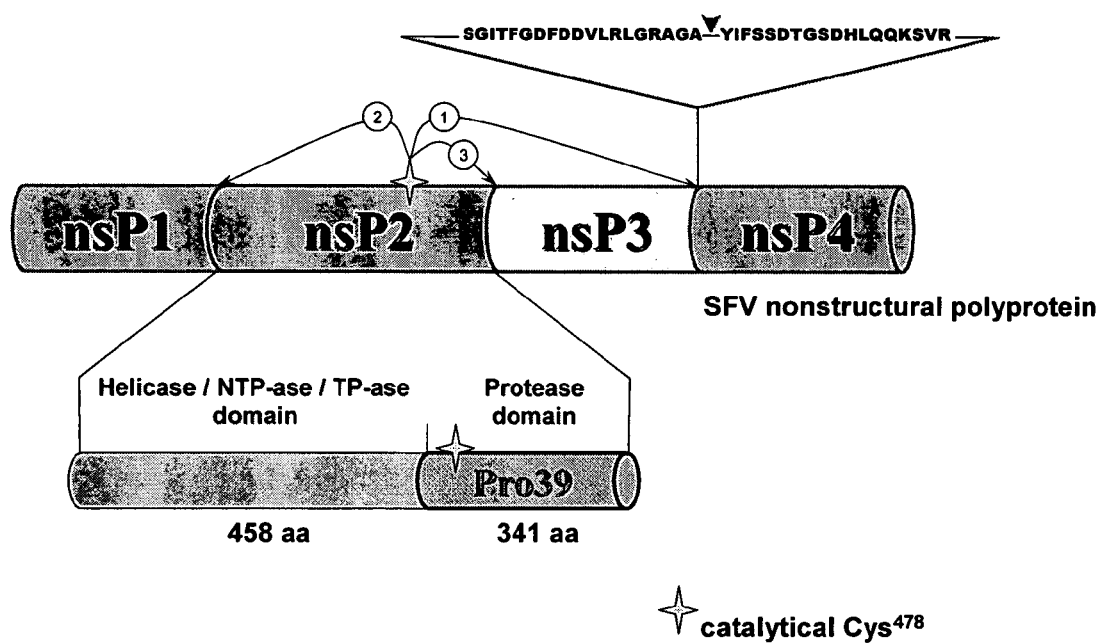
FIG. 1 shows the source of the protease and its recognition sequence. The structure and processing pattern of SFV non-structural polyprotein are shown. Protease recognition sequence (native nsP3/nsP4 site) is given in one letter code; bond cleaved by protease is indicated by arrow. The domain structure of nsP2 protease is shown; asterisk indicates the position of catalytic cystein residue in Pro39 domain.
Figure 2:
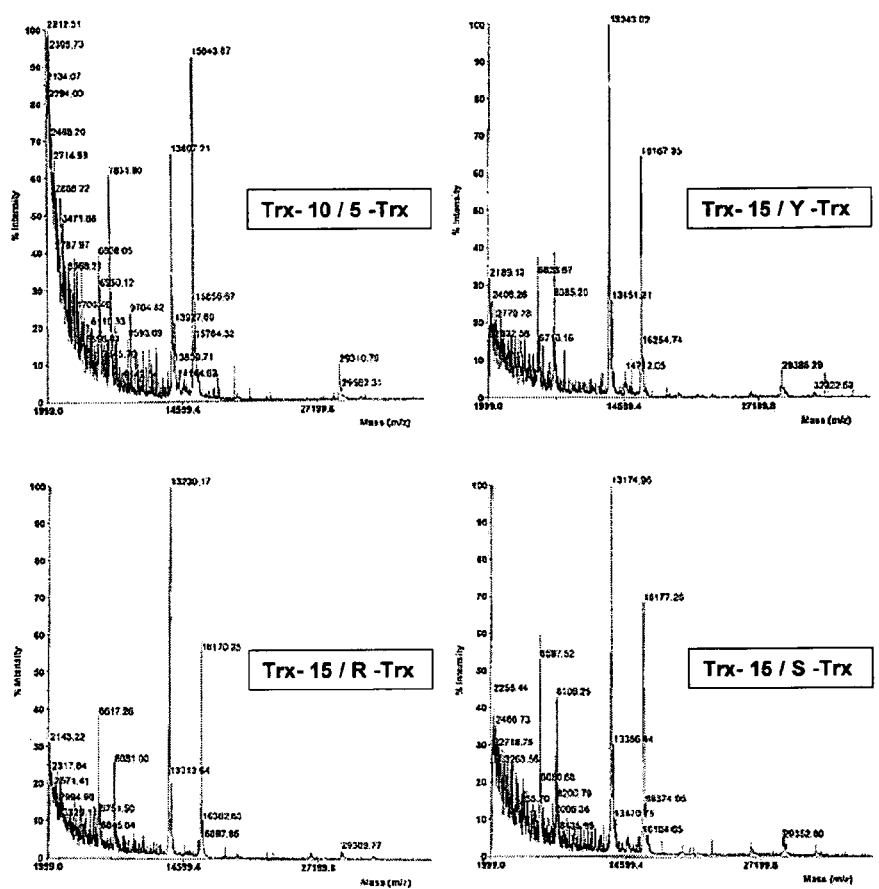
FIG. 2 shows examples of results obtained by mass-spectrometry analysis of the recombinant substrates processed in vitro by Pro39. Analysis was performed by use of MALDI TOF Voyager DE Pro instrument (Applied Biosystem). The names of the substrates are indicated on each panel.

We produced a specific set of expression vectors (for prokaryotic expression and for in vitro translation) for analysis purposes. Extensive analysis was preformed using both in vitro translated substrates as well as substrates expressed in *E. coli* and purified as recombinant proteins by using Ni-NTA chromatography. Using crude deletion analysis we successfully demonstrated that the recognition site for the Pro39 can be considerably shortened. This shortening of recognition sequence eventually led to gradual decrease on the processing efficiency and was used for preliminary mapping of essential sequences. The precise mapping of the essential sequences was made by construction of the protease recognition sequence variants from synthetic oligonucleotides. The cleavage efficiency of the artificial protease substrates, selected as results of this procedure, was somewhat lower than for substrates containing the full-size 19/18 recognition site, but markedly it was high enough to enable protease to process over 10-fold molar excess of substrate within one hour. MALDI-TOF mass-spectrometry showed that the cleavage specificity surprisingly was also maintained for these truncated sites (FIG. 2 first panel). These sequences of detected active recognition site variants are among preferred embodiments of the invention and are as follows:

```
1. (-10)DVLRLGRAGA(↓)YIFSS (+5),    (SEQ ID NO:1)
   designated as 10/5 site 2. (-6)LGRAGA(↓)YIFSS (+5);         (SEQ ID NO:2)
   designated as 6/5 site.
```

The intermediate variants, containing 9, 8 or 7 aa from the nsP3 region (upstream region with the respect of cleavage point) were cleaved specifically but with significantly lower efficiency (FIG. 3). Based on the fact that longer sequences are able to become organized into an alpha helical structure we conclude that one preferred embodiment according to the present invention is an expression vector design having an alpha-helical region in the protease recognition site. Another preferred embodiment is insertion of a protease recognition site with an alpha-helical region into a recombinant protein to be cleaved. These embodiments are supported also with the data shown in FIG. 6, where non structured Ter substrate is poorly cleaved while Trx substrate is effectively cleaved.

Multiple biotechnological approaches require production of proteins with native N-terminus which, quite often, starts with an amino acid different from methionine. The same applies for processing proteins in in vitro conditions with the aim to produce stabilized or destabilized proteins (use of the N-end rule in cell). This approach can serve as powerful approach to create conditional protein knockout (protein will be destabilized and rapidly degraded after removal of stabilizing amino acids from its N-terminus) or knock-in constructs (recombinant protein will be stabilized after removal by protease destabilizing elements like pest-sequences or ubiquitine fusion part). To obtain the recombinant proteins or their subdomains with native N-terminal residues there is a need for a protease being able to cleave specifically substrates with any amino acid residue at its N-terminus (in other words, all elements required for protease site recognition and protease activity should be located upstream from the cleavage point). At the same time site specificity should be maintained. The invention according to the present disclosure is applicable to these approaches.

Figure 4A:
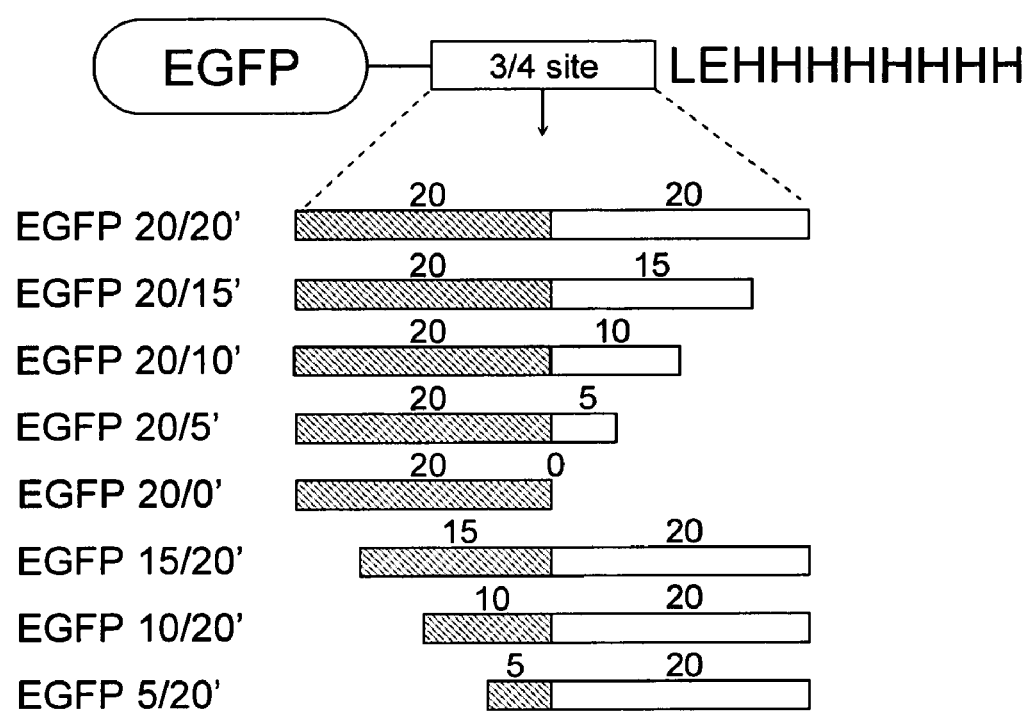
FIG. 4A shows the structure of the recombinant substrates used for analyzing the role of upstream and downstream regions in processing of the ¾ site. EGFP indicates Enhanced Green Florescent Protein. Upstream regions of the cleavage sites are shown as shadowed boxes, and downstream regions as clear boxes. The C-terminus of all substrates contains a Leu-Glu dipeptide followed by 8× His tag. The arrow indicates the position of the cleavage.
Figure 5A:
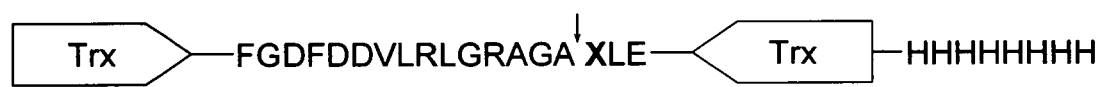
FIG. 5A shows a schematic structure of the recombinant substrate used for analysis of the role of the P1' (position 1) residue in processing of the ¾ site. Trx indicates thioredoxin tag, and the amino acid sequence surrounding the cleavage site is given in one letter code. Amino acid residue at position P1' is indicated with boldface X. Arrow indicates the position of Pro39 cleavage.
Figure 5B:
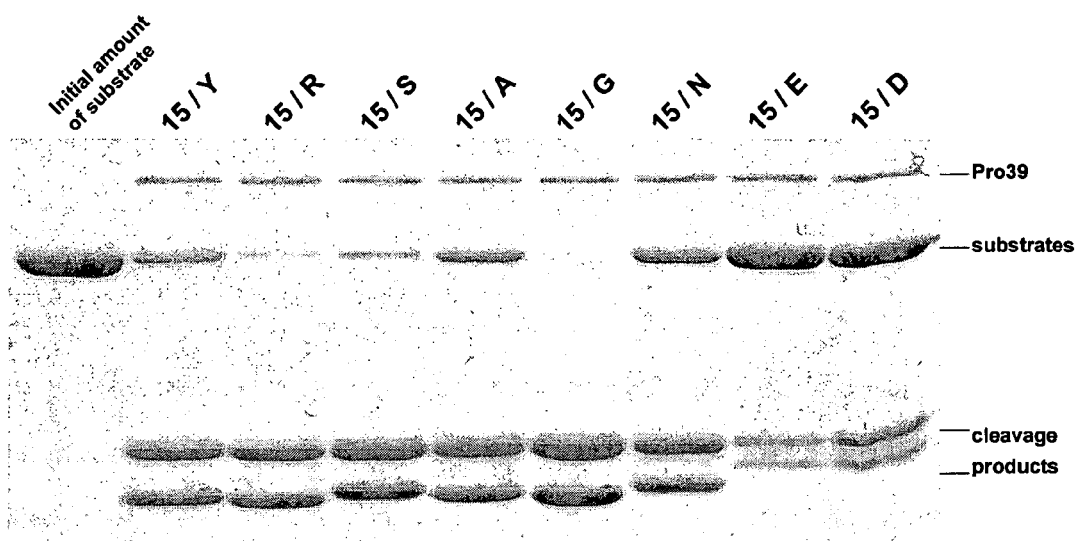
FIG. 5B demonstrates effect of random mutagenesis of downstream amino acid residue P1' (position 1) for processing of the ¾ site. Pro39 digestion of substrates as illustrated in FIG. 5A with different amino acid residues at position P1' of the ¾ site were used. Purified substrates were incubated with Pro39 for 60 minutes at 30° C. in molar ratio 20:1. Reaction products were analyzed by SDS-PAGE and visualized by Coomassie Blue staining. The amino acid residue at position P1' is indicated at the top of the panel. Lane 1 contains the control substrate with no Pro39 added. The positions of Pro39, substrates, and cleavage products are indicated on the right hand side of the blot.

We performed a two step functional analysis and found out that recognition sequence of Pro39 and the corresponding enzyme meet the criteria set forth above. First, deletion mutagenesis of the protease recognition consensus downstream region was carried out. This experiment showed that the downstream region is not needed for cleavage as such to take place, only the cleavage efficiency was affected (FIGS. 4A and B). When the downstream region was substituted with His-tag repeat containing two amino acids (-LEHHH-HHHHH-SEQ ID NO: 9) introduced by XhoI restriction cloning procedure only the cleavage efficiency was affected. Secondly, the extensive site-directed mutagenesis of +1 amino acid residue was carried out. The oligonucleotide derived constructs encoding protease recognition site in configuration +15/X (where X indicates the variable amino acid residue) were cloned into vectors, expressing recombinant substrates. We demonstrated by using expressed and purified substrates that the N-terminal amino acid residue of the protease recognition site can be substituted from Y (tyrosine) to virtually any type of amino acids (S, G, R, N, D, E, C, M, V, L and A) except P without any change of protease cleavage specificity (FIG. 2 and FIG. 5). Most importantly, these experiments clearly indicated that if the native +1 amino acid residue Y (tyrosine) was substituted with S (serine), R (arginine) or G (glycine) residues the cleavage site recognition and/or processing efficiency was significantly enhanced (FIG. 5). This finding also indicates that other residues of the cleavage consensus are useful for the cleavage activity and opens possibility for future selection of high-efficiency cleavage consensuses.

This disclosure shows that artificial truncated substrates with altered +1 amino acid residues were efficiently recognized and actively processed by Pro39 . When activating (G, S or R) amino acids were used as +1 amino acid residues, the processing was more rapid and complete as compared to substrates where wild type truncated sites where used. At the same time the rule that the most efficient cleavage required 10 or 6 native upstream amino acid residues remained unchanged. This led us to conclude that following variants of the highly effective protease recognition sites are among preferred embodiments of the invention:

```
3. (-10)DVLRLGRAGA(↓)RIFSS (+5),    (SEQ ID NO:3)
   designated as 10/R5 site 4. (-6)LGRAGA(↓)RIFSS (+5);         (SEQ ID NO:4)
   designated as 6/R5 site
```

-continued

```
5. (-10)DVLRLGRAGA(↓)GIFSS (+5),      (SEQ ID NO:5)
   designated as 10/G5 site 6. (-6)LGRAGA(↓)GIFSS (+5);           (SEQ ID NO:6)
   designated as 6/G5 site 7. (-6)LGRAGA(↓)SIFSS (+5);           (SEQ ID NO:32)
   designated as 6/S5 site 8. (-10)DVLRLGRAGA(↓)SIFSS (+5),      (SEQ ID NO:33)
   designated as 10/S5 site
```

Importantly, cleavage specificity was preserved for all of these modified recognition sites (demonstrated by mass-spectrometry). All this leads us to conclude that one preferable embodiment of the present invention includes insertion of 10/0 or 6/0 recognition sites into a recombinant protein for protease cleavage with Pro39 so that:

- alpha-helical region of the protease recognition site is preserved
- the +1 position of the newly inserted cleavage consensus most preferably is G, S or R residue and preferably also T or K residue (processing product will have these aa residues at its N-terminus),
- +1 position of the newly inserted cleavage consensus may also be any other residue than P, D or E provided that more protease units are used to obtain the same cleavage efficiency.

Figure 6A:
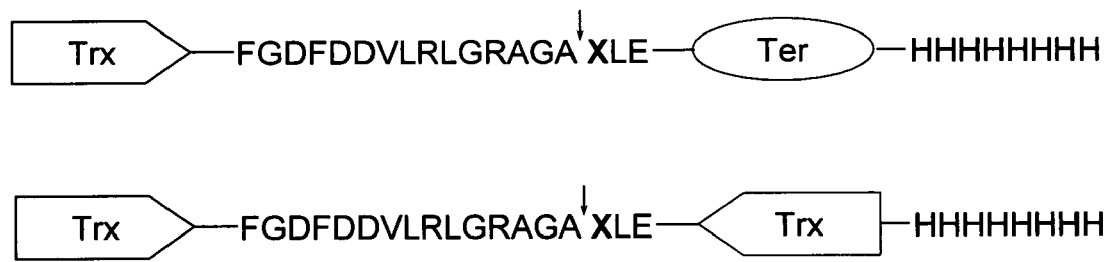
FIG. 6A shows schematic structures of the recombinant substrates used for demonstrating that Pro39 prefers substrates where recognition sequence is placed between two highly structured protein domains. Trx indicates thioredoxin tag, Ter indicates the non-structured truncated Trx tag. Arrow indicates the position of Pro39 cleavage.
Figure 6B:
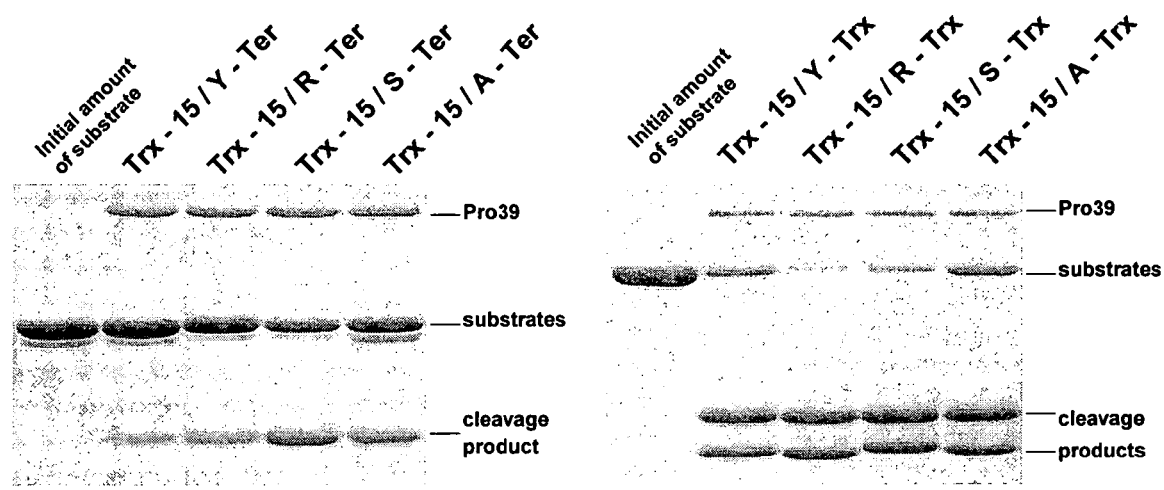
FIG. 6B demonstrates Pro39 digestion of substrates as illustrated in FIG. 5A with one structured tag (left panel) and with two structured tags (right side panel). Purified substrates were incubated with Pro39 for 60 minutes at 30° C. in molar ratio 20:1. Reaction products were analyzed by SDS-PAGE and visualized by Coomassie Blue staining. The name of substrate is indicated at the top of each lane. Lane 1 on both panels contains the control substrate with no Pro39 added. Positions of Pro39, substrates and cleavage products are indicated on the right hand side of the blot.

Two sets of recombinant proteins with inserted protease sites were used for studying the ability of Pro39 to process the modified recognition sites positioned differently in recombinant target protein:

1. recombinant protein consisted of two full size thioredoxine domains and modified protease recognition site between them (shown in FIG. 6A). In this case the protease recognition site is positioned between two compact protein domains (each with size approximately 100 aa residues).
2. recombinant protein consisted of full size thioredoxine domain (compact structure) followed by protease recognition site and truncated C-terminal region (40 aa residues) of thioredoxin (non-structured domain) (shown in FIG. 6A). In this case protease recognition site is positioned between compact N-terminal domain and non-structural smaller C-terminal domain.

Positioning of the recognition sequence between highly structured thioredoxine domains did not cause the decrease of protease cleavage efficiency, but surprisingly on the contrary, the cleavage efficiency was significantly enhanced as compared to cleavage of recognition sites placed between structured and non-structured protein sequences (FIG. 6B) Signals were visualized using bromoclhoroindolyl phosphate/nitro blue tetrazolium (BCIP/NBT). Therefore, according to one preferred embodiment of the current invention modified recognition site for Pro39 can be used for removal of large and structured protein tags such as thioredoxine, GST, MBP or CBP from recombinant proteins. According to another preferred embodiment modified recognition site(s) for Pro39 can be inserted into recombinant protein sequence and the recombinant protein can subsequently be processed into subdomains with desired sizes.

Figure 7A:
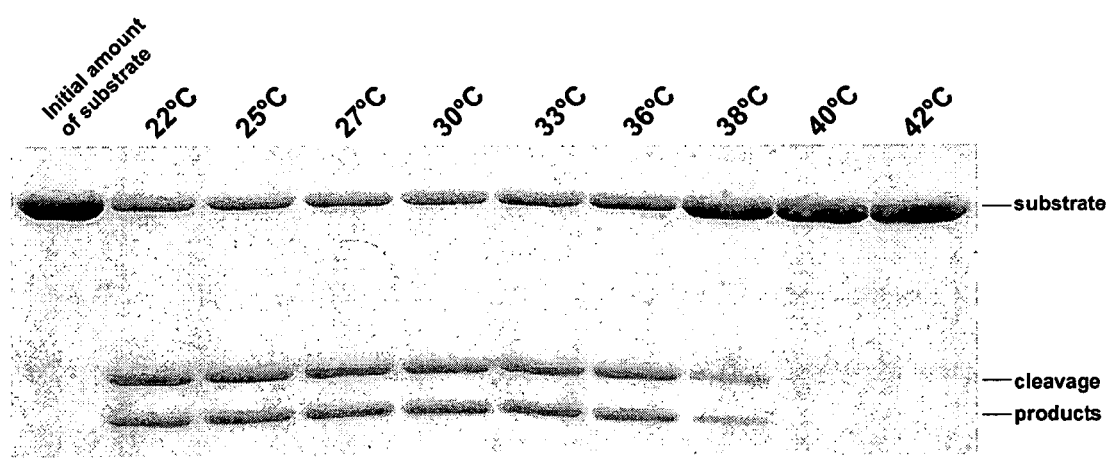
FIG. 7 illustrates the effects of cleavage conditions for processing of the modified recognition sites by Pro39. The substrate used in this experiment was Trx fused with 10/5 recognition site.
Figure 11:

A still another aspect the present invention provides the conditions for use of the Pro39 for cleavage of the recombinant proteins containing the modified recognition sequences. This is essential part of the invention, since there has been an unmet need for a protease operable in wide range of conditions. A wide variety of conditions was tested to estimate stability of Pro39 and its preferences for cleavage of recombinant substrates. According to this disclosure Pro39 cleaves these substrates in wide temperature range including low temperatures with temperature optimum around 30° C. (FIGS. 7A and 11). An important aspect of this invention is that substrates with modified recognition sites can be cleaved by Pro39 at +4° C. property which may be highly useful for processing of delicate and temperature sensitive recombinant proteins. Cleavage activity was maintained also at as high temperature as 39° C. but with greatly reduced efficiency (FIG. 7A).

Figure 7B:
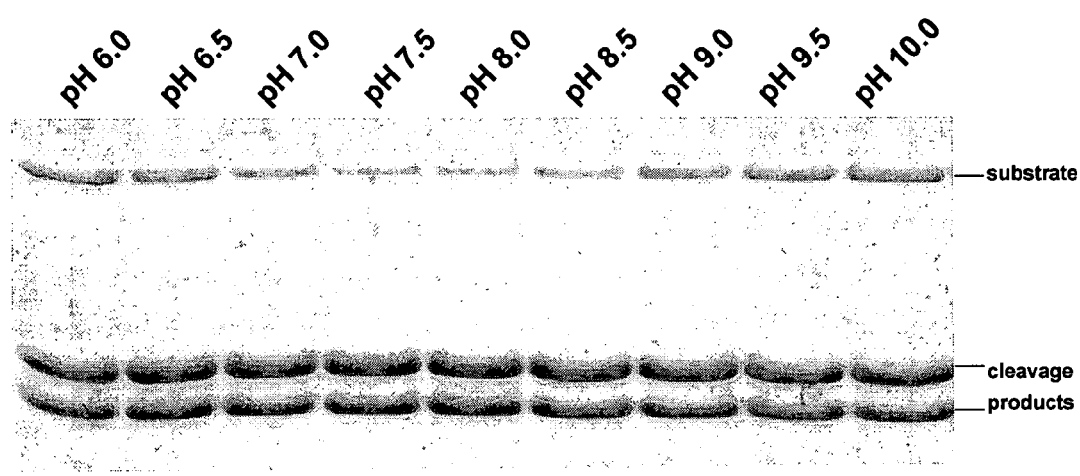

Pro39 cleaves the substrates in neutral pH region (FIG. 7B) in most commonly used buffer systems, including Tris, HEPES and phosphate buffers. The pH optimum was detected to be about 7.5–8.0 and the HEPES buffer as the most suitable buffer for maximal cleavage efficiency.

Pro39 cleaves these substrates at the presence of high concentration of NaCl (up to 4 M) or urea (up to 1.5 M) (FIGS. 8A and B). This feature is important because it allows protease cleavage in conditions where protein-protein interactions are minimized (high NaCl concentrations). For example this includes cleavage of the substrates purified by immuno-absorption chromatography or ion-exchange chromatography without previous desalting of the eluted proteins. Capability to cleave in presence of high concentration of urea can be used for cleavage of partially denatured (or renatured) proteins. This can be important if the protease site is not opened for cleavage under native conditions.

Figure 9:
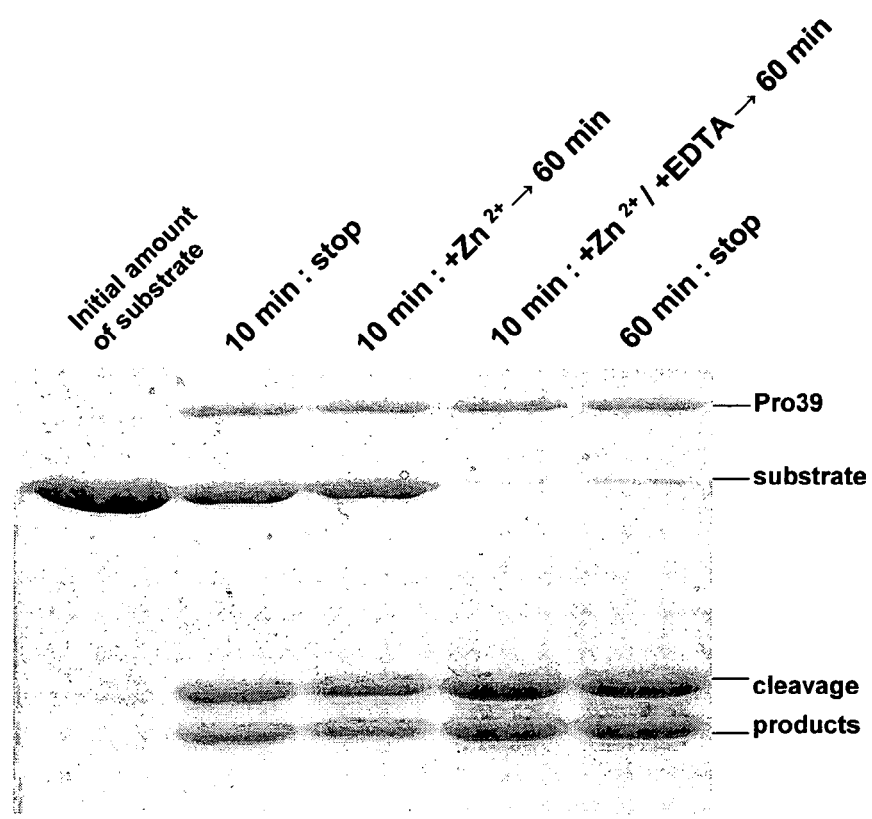

Cleavage of these substrates by Pro39 can be reversibly inhibited by addition of Zn-ions and re-activated by addition of EDTA. Low concentration of Zn-ions cause rapid and complete block of the processing, removal of Zn-ions activates the processing (FIG. 9.). This property can be used to block premature or unwanted processing of recombinant proteins. This also indicates that addition of EDTA is needed for the cleavage buffer to remove endogenous inhibitors of protease activity. For that it was demonstrated the EDTA does not suppress processing by Pro39 even at high concentrations (up to 100 mM).

Pro39 cleaves these substrates both in liquid phase as well as in resin-bound state on the immuno-absorption column (FIG. 11–15). This allows easy performance of the protease reaction as well as simple separation of the cleaved products for unprocessed material.

The invention can be better understood by way of the following examples which are representative of the preferred embodiments thereof, but which are not to be construed as limiting the scope of the invention.

EXAMPLE 1

Construction of Vectors for Expression of Recombinant Proteins in Mammalian Cells Vector 1 was designed based on the vector pQM-CMV-E2-N-A-int (Quattromed Ltd. P1-114-020). Full sequence of the vector is shown in FIG. 18. The design of vector 1 is shown in FIG. 16. Full sequence of the This vector was designed so that it allows both precise positioning of the N-terminus of recombinant protein into +1 position of protease cleavage site as well as cloning downstream of the +5 position of modified protease consensus for higher efficiency of the cleavage. Introduction of cleavage site Pdi1 changes +1 residue in protease recognition site to G, but does not change invariant position of −1. The sequence of the protease recognition site in this vector is thereby according to SEQ ID NO: 5.

Vector 2 is designed for cloning of recombinant protein expressing gene downstream of optimized 10/R5 cleavage site for maximally efficient cleavage of recombinant protein. The vector is based on vector pQM-CMV-E2-N-A-int (Quattromed Ltd.). Full sequence of the vector is shown in FIG. 18. The design of vector 2 is shown in FIG. 17. The CGC codon for arginine (underlined in the figure) is designed to activate the cleavage of recombinant protein. The protease recognition site in this vector is according to SEQ ID NO:3.

EXAMPLE 2

Design of Insertion Elements which can be Used in QM-CMV-E2-N-A-intvector (Quattromed Ltd. Catalog Number P1-114-020) Based Constructs and/or Directly Inserted into Chosen Position of Recombinant Protein Using Site-specific Mutagenesis Cassette designs are based on the use of optimized 10/R5 or 6/R5 sites (SEQ ID NO: 3 and SEQ ID NO: 4, respectively). These sites can be inserted into expression vector or introduced directly into recombinant protein encoding sequence by site directed mutagenesis:

```
10/R5
5' GAC GTC CTG CGA CTA GGC CGC GCG GGT GCC CGC ATT TTC TCC TCG 3'

3' CTG CAG GAC GCT GAT CCG GCG CGC CCA CGG GCG TAA AAG AGG AGC 5'

D   V   L   R   L   G   R   A   G   A   R   I   F   S   S   G
```

Construct was made by using oligonucleotides:

```
5'GA TCT GAC GTC CTG CGA CTA GGC CGC GCG GGT GCC CGC ATT TTC TCC TCG GGA TCC A

3'A CTG CAG GAC GCT GAT CCG GCG CGC CCA CGG GCG TAA AAG AGG AGC CCT AGG TTC GA
```

Oligos were annealed and cloned into the vector pQM-CMV-E2-N-A-int, digested with restrictases BamHI and HindIII. The underlined GCG codon codes for arginine, which activates the cleavage of recombinant protein.

Oligos were annealed and cloned into the vector pQM-CMV-E2 N-Aint, digested with restrictases BamHI and HindIII. The underlined GCG codon codes for arginine, which activates the cleavage of recombinant protein.

The insertion strategy is also usable for non-optimized 10/0 and 6/0 type cassettes, which can be used for production of cleavage products with exact N-terminal amino acid residues.

Cassette designs are based on the use of use non-optimized 10/0 or 6/0 sites which can be inserted into expression vector or introduced directly into recombinant protein encoding sequence by site directed mutagenesis.

```
10/0
5' GAC GTC CTG CGA CTA GGC CGC GCG GGT GCC 3'

3' CTG CAG GAC GCT GAT CCG GCG CGC CCA CGG 5'

D   V   L   R   L   G   R   A   G   A
```

Construct was made by using oligonucleotides:

```
5'GA TCT GAC GTC CTG CGA CTA GGC CGC GCG GGT GCC CGC GGA TCC A

3'A CTG CAG GAC GCT GAT CCG GCG CGC CCA CGG GCG CCT AGG TTC GA
```

```
6/R5
5' CTA GGC CGC GCG GGT GCC CGC ATT TTC TCC TCG 3'

3' GAT CCG GCG CGC CCA CGG GCG TAA AAG AGG AGC 5'

L   G   R   A   G   A   R   I   F   S   S   G
```

Construct was made by using oligonucleotides:

```
5'GA TCT CTA GGC CGC GCG GGT GCC CGC ATT TTC TCC TCG GGA TCC A

3'A GAT CCG GCG CGC CCA CGG GCG TAA AAG AGG AGC CCT AGG TTC GA
```

Oligonucleotides were annealed and cloned into the vector pQM-CMV-E2-N-A-int, digested with restrictases BamHI and HindIII.

6/0
5' CTA GGC CGC GCG GGT GCC 3'

3' GAT CCG GCG CGC CCA CGG 5'

L   G   R   A   G   A

Construct was made using oligonucleotides:

5'GA TCT CTA GGC CGC GCG GGT GCC GGA TCC A

3'A GAT CCG GCG CGC CCA CGG CCT AGG TTC GA

Oligonucleotide were annealed and cloned into the pQM-CMV-E2-N-Aint, digested with restrictases BamHI and HindIII.

EXAMPLE 3

Identification of the Minimal Cleavage Consensus of Pro 39 Using Deletion Mutagenesis The analysis of the cleavage consensus requirements was made as a two step experiment. First, the set of constructs, expressing recombinant proteins with truncated protease recognition sites were made. For this purpose the green fluorescent protein was fused with following truncated cleavage consensus elements constructed by PCR:

20/20 site (control, previously reported to serve as excellent substrate for Pro39 ), encoding the recognition peptide with SEQ ID NO:10 as follows:

```
S G I T F G D F D D V L R L G R A G A ↓ Y I F S S D T G S G H L Q Q K S V R
·         ·         ·         ·       · ·       ·         ·         ·     ·
-19     -15       -10        -5      -1 +1     +5       +10       +15   +18
```

15/20 site (construct 1) encoding the recognition peptide with SEQ ID NO:11 as follows:

```
F G D F D D V L R L G R A G A ↓ Y I F S S D T G S G H L Q Q K S V R
·         ·         ·       · ·       ·         ·         ·     ·
-15     -10        -5      -1 +1     +5       +10       +15   +18
```

10/20 site (construct 2) encoding the recognition peptide with SEQ ID NO:12 as follows:

```
D V L R L G R A G A ↓ Y I F S S D T G S G H L Q Q K S V R
·         ·       · ·       ·         ·         ·     ·
-10      -5      -1 +1     +5       +10       +15   +18
```

5/20 site (construct 3) encoding the recognition peptide with SEQ ID NO:13 as follows:

```
G R A G A ↓ Y I F S S D T G S G H L Q Q K S V R
·       · ·       ·         ·         ·     ·
-5     -1 +1     +5       +10       +15   +18
```

20/15 site (construct 4) encoding the recognition peptide with SEQ ID NO:14 as follows:

```
S G I T F G D F D D V L R L G R A G A ↓ Y I F S S D T G S G H L Q Q K
·         ·         ·         ·       · ·       ·         ·         ·
-19     -15       -10        -5      -1 +1     +5       +10       +15
```

20/10 site (construct 5) encoding the recognition peptide with SEQ ID NO:15 as follows:

```
S G I T F G D F D D V L R L G R A G A ↓ Y I F S S D T G S G
·         ·         ·         ·       · ·       ·         ·
-19     -15       -10        -5      -1 +1     +5       +10
```

20/5 site (construct 6) encoding the recognition peptide with SEQ ID NO:16 as follows:

```
S  G  I  T  F  G  D  F  D  D  V  L  R  L  G  R  A  G  A ↓ Y  I  F  S  S
-19         -15         -10         -5            -1 +1       +5
```

20/0 site (construct 7) encoding the recognition peptide with SEQ ID NO:17 as follows:

```
   S  G  I  T  F  G  D  F  D  D  V  L  R  L  G  R  A  G  A ↓ (LE)HHHHHHHH
  -19         -15         -10         -5            -1
```

The eight substrates (green fluorescent protein fused with the eight recognition site variant given above) are schematically illustrated also in FIG. 4A.

Figure 4B:
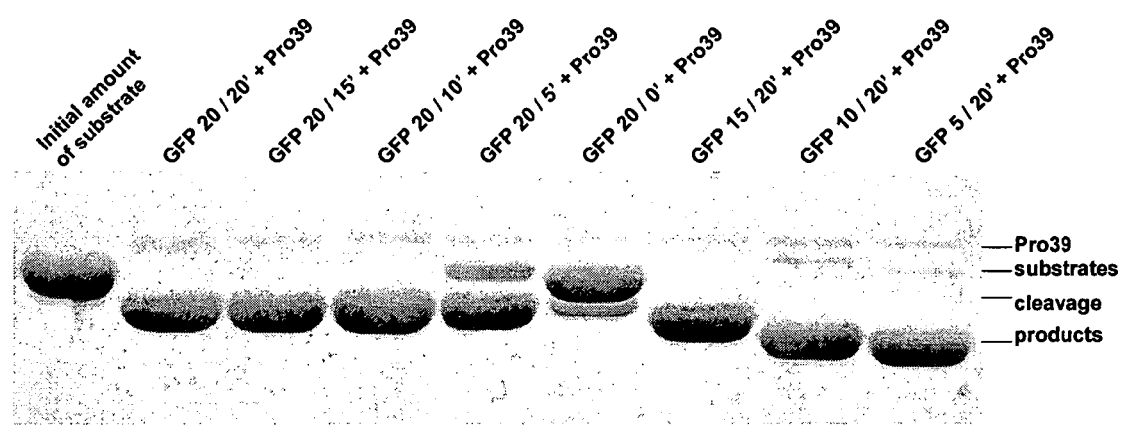
FIG. 4B demonstrates the role of upstream and downstream regions of the processing of the ¾ site. Recombinant substrates illustrated in FIG. 4A were used for the cleavage. Purified substrates were incubated with Pro39 for 60 minutes at 30° C. in molar ratio 20:1. Reaction products were analyzed by SDS-PAGE and visualized by Coomassie Blue staining. Substrates are indicated on the top of each lane. Lane 1 contains the control substrate (E2-EGFP 20/20') with no Pro39 added. Positions of Pro39, substrates and cleavage products are indicated at the right hand side of the blot.

All eight substrates were expressed in *E. coli* and purified as recombinant proteins using Ni-NTA chromatography and subjected to the processing with Pro39. Purified substrates were incubated with Pro39 for 60 minutes at 30° C. in molar ratio 20:1. Reaction products were analyzed by SDS-PAGE and visualized by Coomassie Blue staining. The results clearly demonstrate that the recognition site for the Pro39 can be considerably shortened. Referring to FIG. 4B:

- as little as 5 aa residues from upstream side is needed for the processing to take place. However recombinant protein including construct 3 (5/20 site according to SEQ ID NO: 13) was processed considerably slower than recombinant proteins with 15 or 10 aa residues from the region upstream of the cleavage site.
- no virus specific aa residues were needed on the downstream side for the processing to take place. However, processing of the recombinant protein including construct 7 (20/0 site according to SEQ ID NO: 17) was rather ineffective as compared to that of recombinant proteins including constructs 4, 5, and 6 (20/15 site according to SEQ ID NO:14, 20/10 site according to SEQ ID NO:15 and 20/5 site according to SEQ ID NO:16, respectively)

Based on these results we subjected substrates having 15 to 5 aa residues from upstream and 0–5 aa residues from downstream region of the protease recognition site for more detailed analysis.

EXAMPLE 4

Figure 3A:
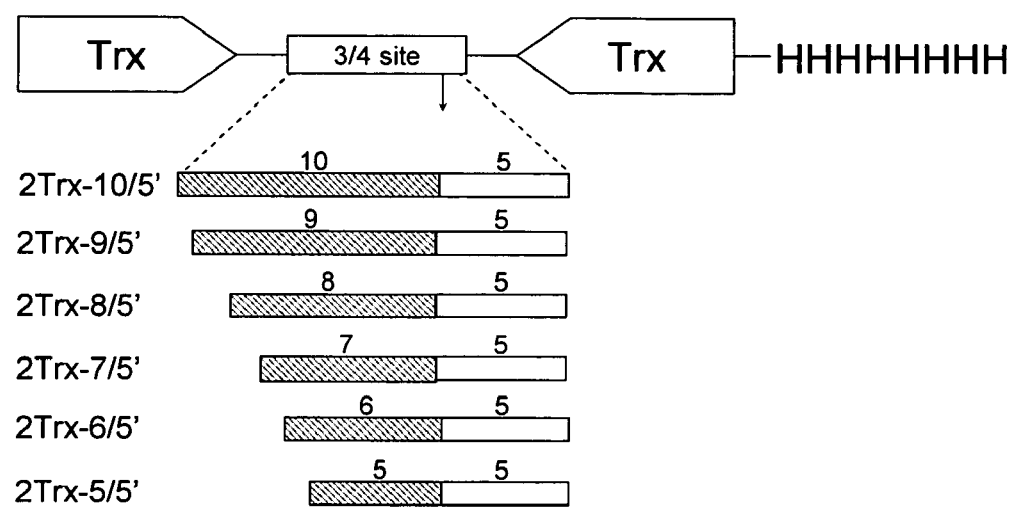
FIG. 3A represents a schematic structure of the recombinant substrates used for determination of influence of the length of upstream region of the ¾ cleavage site on the cleavage efficiency of Pro39. (In the figures the cleavage site is called ¾ cleavage site because in vivo the site is between nsP3 and nsP4).Trx indicates thioredoxin tag. The arrow on the top indicates the position of Pro39 cleavage. HHHHHHHH is a histidine tag used for purification of the substrate.

Identification of the Precise Minimal Cleavage Consensus of Pro 39 Using Oligonucleotide Insertion Mutagenesis The precise mapping of the essential sequences was made by construction of the protease recognition sequence variants from synthetic oligonucleotides. FIG. 3A illustrates schematically the substrates comprising oligonucleotide duplexes, encoding for following cleavage site variants:

10/5 site (construct 8) encoding the recognition peptide with SEQ ID NO:1 as follows:

```
D  V  L  R  L  G  R  A  G  A ↓ Y  I  F  S  S
-10 -9 -8 -7 -6 -5 -4 -3 -2 -1  +1 +2 +3 +4 +5
```

9/5 site (construct 9) encoding the recognition peptide with SEQ ID NO: 18 as follows:

```
V  L  R  L  G  R  A  G  A ↓ Y  I  F  S  S
-9 -8 -7 -6 -5 -4 -3 -2 -1  +1 +2 +3 +4 +5
```

8/5 site (construct 10) encoding the recognition peptide with SEQ ID NO:19 as follows:

```
L  R  L  G  R  A  G  A ↓ Y  I  F  S  S
-8 -7 -6 -5 -4 -3 -2 -1  +1 +2 +3 +4 +5
```

7/5 site (construct 11) encoding the recognition peptide with SEQ ID NO:20 as follows:

```
R  L  G  R  A  G  A ↓ Y  I  F  S  S
-7 -6 -5 -4 -3 -2 -1  +1 +2 +3 +4 +5
```

6/5 site (construct 12) encoding the recognition peptide with SEQ ID NO:2 as follows:

```
L  G  R  A  G  A ↓ Y  I  F  S  S
-6 -5 -4 -3 -2 -1  +1 +2 +3 +4 +5
```

5/5 site (construct 13) encoding the recognition peptide with SEQ ID NO:21 as follows:

```
G  R  A  G  A ↓ Y  I  F  S  S
-5 -4 -3 -2 -1  +1 +2 +3 +4 +5
```

Figure 3B:
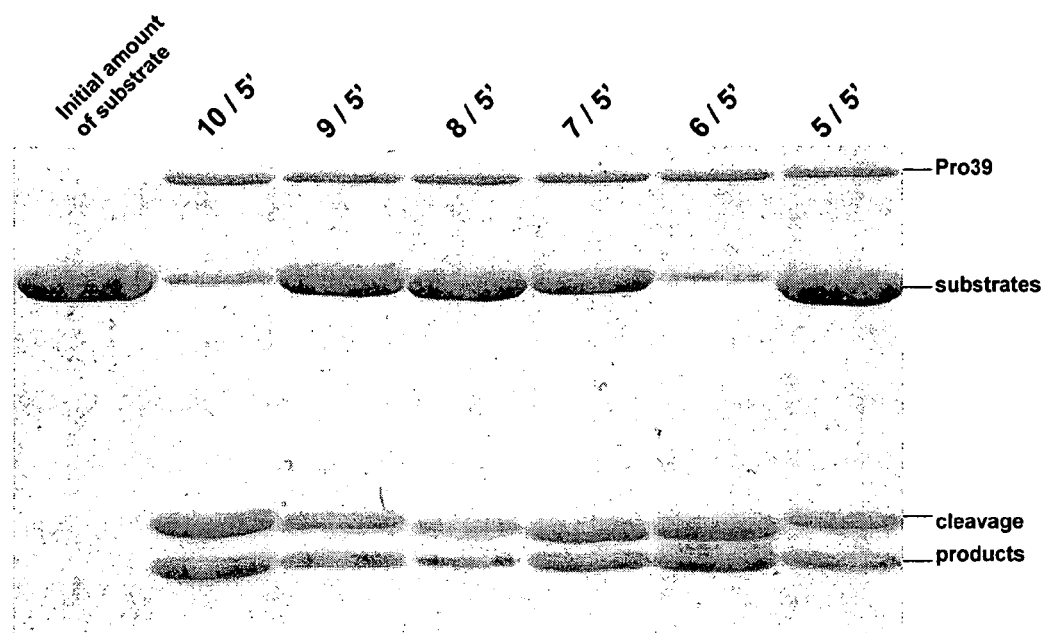
FIG. 3B shows influence of the length of upstream region of the ¾ cleavage site on the cleavage efficiency of Pro39. Recombinant substrates as illustrated in FIG. 3A were used for cleavage. Purified substrates were incubated with Pro39 for 60 minutes at 30° C in molar ration 20:1. Reaction products were analyzed by SDS-PAGE and visualized by Coomassie Blue staining. Substrates are indicated at the top of each lane. Lane 1 contains the control substrate with no Pro39 added. The position of Pro39, substrates and cleavage products are indicated at the right hand side of the blot.

Corresponding recombinant proteins as illustrated in FIG. 3A were expressed in *E. coli*, purified by Ni-NTA chromatography and subjected to the treatment with Pro39. Purified substrates were incubated with Pro39 for 60 minutes at 30° C. in molar ratio 20:1. Reaction products were analyzed by SDS-PAGE and visualized by Coomassie Blue staining. The results are shown in FIG. 3B. The cleavage efficiency of the substrates 8–13 was compared to each other and to the control substrate 0. Two substrates—those containing recognition sites 10/5 and 6/5—were selected as results of this procedure. The cleavage efficiencies observed for corresponding recombinant proteins were somewhat lower than it was observed for control substrate (19/18), but still high enough to enable protease to process completely over than 10-fold molar excesses of substrate within one hour. It was demonstrated by use of the MALDI-TOF mass-spectrometry that cleavage specificity was also maintained for these truncates sites. It was also found that cleavage efficiencies for substrates containing constructs 9, 10, 11, and 13 (SEQ ID NO: 18, 19, 20 and 21, respectively) were significantly lower than those containing constructs 8 and 12 (SEQ ID NO:1 and 2, respectively).

EXAMPLE 5

Identification of the Role of +1 Amino Acid Residue for Cleavage Activity and Specificity. Construction of the Optimized Recognition Sites.

As indicated in examples above Pro39 is capable to process a substrate containing construct 8 (10/5 site according to SEQ ID NO: 1) with no virus-specific sequence located downstream of the cleavage point. To determine if there is any requirement for +1 amino acid residue in substrate for Pro39 recognition and cleavage specificity the protease recognition sequence variants were constructed from synthetic oligonucleotides. FIG. 5A illustrates schematically substrates comprising oligonucleotide duplexes encoding for following cleavage site variants:

15/Y site (construct 14) encoding the recognition peptide with SEQ ID NO: 22 as follows:

```
F G D F D D V L R L G R A G A ↓ Y
-15         -10        -5        -1 +1
```

15/A site (construct 15) encoding the recognition peptide with SEQ ID NO:23 as follows:

```
F G D F D D V L R L G R A G A ↓ A
-15         -10        -5        -1 +1
```

15/G site (construct 16) encoding the recognition peptide with SEQ ID NO: 24 as follows:

```
F G D F D D V L R L G R A G A ↓ G
-15         -10        -5        -1 +1
```

15/R site (construct 17) encoding the recognition peptide with SEQ ID NO:25 as follows:

```
F G D F D D V L R L G R A G A ↓ R
-15         -10        -5        -1 +1
```

15/S site (construct 18) encoding the recognition peptide with SEQ ID NO:26 as follows:

```
F G D F D D V L R L G R A G A ↓ S
-15         -10        -5        -1 +1
```

15/N site (construct 19) encoding the recognition peptide with SEQ ID NO: 27 as follows:

```
F G D F D D V L R L G R A G A ↓ N
-15         -10        -5        -1 +1
```

15/E site (construct 20) encoding the recognition peptide with SEQ ID NO: 28 as follows:

```
F G D F D D V L R L G R A G A ↓ E
-15         -10        -5        -1 +1
```

15/D site (construct 21) encoding the recognition peptide with SEQ ID NO: 29 as follows:

```
F G D F D D V L R L G R A G A ↓ D
-15         -10        -5        -1 +1
```

Corresponding recombinant proteins were expressed in *E. coli*, purified by Ni-NTA chromatography and subjected to the treatment with Pro39. Purified substrates were incubated with Pro39 for 60 minutes at 30° C. in molar ration 20:1. Reaction products were analyzed by SDS-PAGE and visualized by Coomassie blue staining. It was demonstrated that the N-terminal amino acid residue of the protease recognition site can be substituted from Y (tyrosine, construct 14 according to SEQ ID NO: 22) to virtually any type of amino acids (S, G, R, N, D, E, C, M, L and A) except P with no change of protease cleavage specificity. At the same time anomalous electrophoretic mobility was detected for cleavage products with acidic amino acid residues (constructs 20 and 21 according to SEQ ID NO: 28 and 29, respectively) on its N-terminal position; MALDI-TOF analysis of these products clearly indicated that this is not due the unspecific cleavage of corresponding cleavage sites but due some change of mobility during SDS-PAGE. Most importantly, these experiments clearly indicated that if the native +1 amino acid residue Y (tyrosine) was substituted with glycine (G), serine (S) or arginine (R) residues (constructs 16, 17 and 18 according to SEQ ID NO: 24, 25 and 26, respectively) the cleavage site recognition and/or processing efficiently was significantly enhanced.

Oligonucleotide duplexes, encoding for following cleavage site variants were inserted into specially designed vector for expression of the recombinant substrates:

10/S site (construct 22) encoding the recognition peptide with SEQ ID NO:30 as follows:

```
D V L R L G R A G A ↓ S
-10        -5        -1 +1
```

6/S site (construct 23) encoding the recognition peptide with SEQ ID NO: 31 as follows:

```
L G R A G A ↓ S
-6         -1 +1
```

Corresponding recombinant proteins where expressed in *E. coli*, purified by Ni-NTA chromatography and subjected to the treatment with Pro39 as described above. It was demonstrated that recombinant proteins, containing these protease recognition sites, were processed specifically and with higher efficiency that recombinant proteins containing corresponding unmodified sites (result not shown). This finding indicates that modified protease recognition sites can be used in expression vectors instead of unmodified sites.

EXAMPLE 6

Demonstration of Pro39 Cleavage of Substrate Purified on Anti-E2Tag Antibody Conjugated Sepharose Resin Recombinant protein TAP-DBD (FIG. 10A) was expressed in *E. coli*. Cells were lysed under native conditions. *E. coli* cell lysate was clarified and loaded onto pre-equilibrated anti-E2Tag antibody conjugated Sepharose resin. Substrate binding to resin was performed at 8° C. for 2,5 h. Subsequent washes of the column with buffer containing 1M NaCl and 100 mM NaCl removed contaminating proteins from column. Anti-E2Tag antibody conjugated Sepharose resin -bound substrate TAP-DBD was eluted under low pH conditions (0,5% acetic acid), pH neutralizing followed with 1 M Tris pH 9,5. Eluted substrate was incubated with Pro39 at 30° C. for various times. Reaction products were analyzed by Western Blot method using anti-E4Tag antibody 1E2. Goat anti-mouse IgG alkaline phosphatase conjugate was used as secondary antibody. Signals were visualized using bromochloroindolyl phosphate/nitro blue tetrazolium (BCIP/NBT). The results are shown in FIG. 10B and it can be clearly seen that the substrate is cleaved after incubation of 2 hours.

EXAMPLE 8

Celavage of Column-bound Substrate by Pro39.

Recombinant protein TAP-DBD (FIG. 10A) was expressed in *E. coli*. Cells were lysed under native conditions. *E. coli* cell lysate was clarified and loaded onto pre-equilibrated anti-E2Tag antibody conjugated Sepharose resin. Substrate binding to resin was performed at 8° C. for 2,5 h. Subsequent washes of the column with buffer containing 1M NaCl and 100 mM NaCl removed contaminating proteins from column. Column-bound substrate was cleaved by incubating with Pro39 at 30° C. for 3 h. The flow through fraction was collected after cleavage. The cleaved product was eluted using buffer containing 1M NaCl. Uncleaved and still column-bound cleaved substrate was eluted using 2×Laemmli buffer. Cleavage products or eluted proteins were analyzed by Western Blot method using anti-E2Tag antibody (FIG. 13) and anti-E4Tag antibody (FIG. 12). Goat anti-mouse IgG alkaline phosphatase conjugate was used as secondary antibody. Signals visualized using bromochloroindolyl phosphate/nitro blue tetrazolium (BCIP/NBT).The result clearly reveals that the pro39 works in column; it cleaves the matrix boind protien not only in solution but alos on the packed column.

A control experiment was performed in order to show that column-bound substrate is not cleaved without Pro39. Recombinant protein TAP-DBD (FIG. 10A) was expressed in *E. coli*. Cells were lysed under native conditions. *E. coli* cell lysate was clarified and loaded onto pre-equilibrated anti-E2Tag antibody conjugated Sepharose resin. Substrate binding to resin was performed at 8° C. for 2,5 h. Subsequent washes of the column with buffer containing 1 M NaCl and 100 mM NaCl removed contaminating proteins from column. Column-bound substrate was incubated with buffer without Pro39 under the same conditions at 30° C. for 3 h as with Pro39 above. The flow through fraction collected after cleavage. Elution using buffer containing 1M NaCl performed and elution with 2×Laemmli buffer followed. Reaction products were analyzed by Western Blot method using anti-E4Tag antibody 1E2 (FIG. 14) and anti-E2Tag antibody (FIG. 15). Goat anti-mouse IgG alkaline phosphatase conjugate as secondary antibody was used. Signals visualized using bromochloroindolyl phosphate/nitro blue tetrazolium (BCIP/NBT). As clearly seen from the blots of FIGS. 14 and 15 the substrate was not cleaved.

What is claimed is:

1. An isolated nucleic acid sequence encoding a protease recognition site, wherein the recognition site consists of the amino acid sequence selected from the group consisting of SEQ ID NO:3, SEQ ID NO:4, SEQ ID NO:5, SEQ ID NO:6, SEQ ID NO:32 and SEQ ID NO:33 and wherein the nucleic acid sequence is derived from Semliki Forest Virus nonstructural polyprotein sequence and wherein the protease recognition site allows protein cleavage with Pro39.

2. An expression vector comprising a coding sequence for a fusion protein, said coding sequence further comprising:
   a) a first nucleotide sequence encoding a protease recognition site, said recognition site having an amino acid sequence selected from the group consisting of SEQ ID NO: 3, SEQ ID NO: 4, SEQ ID NO: 5, SEQ ID NO: 6, SEQ ID NO: 32 and SEQ ID NO: 33 and said recognition site further allowing cleavage of the fusion protein with Pro39; and b) a second nucleotide sequence encoding for a protein of interest.

3. The vector according to claim 2, wherein the protein of interest is a protein used for pharmaceutical purposes.

4. The vector according to claim 2, wherein the vector is capable of expressing the fusion protein in E.coli.

5. The vector according to claim 2, wherein the vector is capable of expressing the fusion protein in a mammalian cell.

6. The vector according to claim 2, wherein the vector is capable of expressing the fusion protein in a yeast cell.

7. A method for obtaining a substantially pure protein of interest, said method comprising the steps of:
   a. providing a fusion protein, said fusion protein further comprising a protease recognition site, said recognition site consisting of amino acid sequence selected from the group consisting of SEQ ID NO:3, SEQ ID NO:4, SEQ ID NO:5, SEQ ID NO:6, SEQ ID NO: 32 and SEQ ID NO: 33; and
   b. treating the fusion protein with Pro39 under conditions allowing cleavage of said protein of interest from said fusion protein.

8. The method according to claim 7, wherein the method is used to remove peptide or protein tags from the fusion protein.

9. The method according to claim 7, wherein the treating conditions with Pro39 include sodium chloride concentrations up to 4M or urea concentrations up to 1.5M.

10. The method according to claim 7, wherein the treating conditions with Pro39 includes treating on a column resin.

11. The method according to claim 7, wherein the treating conditions with Pro39 include temperatures between 40° C and 39° C.

12. The method according to claim 11, wherein the temperature is 30° C.

13. The method according to claim 7, wherein the treating conditions with Pro39 include pH between 6 and 10.

14. The method according to claim 13, wherein the treating conditions with Pro39 include pH between 7.5 and 8.0.

15. An isolated and purified amino acid sequence for use as a protease recognition site allowing protein cleavage with Pro39, said amino acid sequence further being selected from the group consisting of SEQ ID NO:3, SEQ ID NO:4, SEQ ID NO:5, SEQ ID NO:6, SEQ ID NO:32 and SEQ ID NO:33.

* * * * *